(12) United States Patent
Aggarwal

(10) Patent No.: US 7,462,646 B2
(45) Date of Patent: *Dec. 9, 2008

(54) OSTEOCLASTOGENESIS INHIBITORS AND USES THEREOF

(75) Inventor: Bharat B. Aggarwal, Houston, TX (US)

(73) Assignee: Research Development Foundation, Carson City, NV (US)

( * ) Notice: Subject to any disclaimer, the term of this patent is extended or adjusted under 35 U.S.C. 154(b) by 347 days.

This patent is subject to a terminal disclaimer.

(21) Appl. No.: 10/925,608

(22) Filed: Aug. 25, 2004

(65) Prior Publication Data

US 2005/0080023 A1    Apr. 14, 2005

Related U.S. Application Data

(60) Provisional application No. 60/497,841, filed on Aug. 26, 2003.

(51) Int. Cl.
*A61K 31/12*   (2006.01)
*A61K 31/56*   (2006.01)
*A61K 31/225*  (2006.01)

(52) U.S. Cl. .................. 514/679; 514/171; 514/177; 514/548

(58) Field of Classification Search .............. None
See application file for complete search history.

(56) References Cited

U.S. PATENT DOCUMENTS

| | | | |
|---|---|---|---|
| 4,427,649 A | 1/1984 | Dingle et al. | 514/318 |
| 5,049,388 A | 9/1991 | Knight et al. | 424/450 |
| 5,401,777 A | 3/1995 | Ammon et al. | 514/731 |
| 5,494,668 A | 2/1996 | Patwardhan | 424/756 |
| 5,861,415 A | 1/1999 | Majeed et al. | 514/321 |
| 5,891,924 A | 4/1999 | Aggarwal | 514/679 |
| 5,925,376 A | 7/1999 | Heng | 424/451 |
| 5,958,378 A | 9/1999 | Waldrep et al. | 424/45 |
| 6,090,407 A | 7/2000 | Knight et al. | 424/450 |
| 6,106,859 A | 8/2000 | Densmore, Jr. et al. | 424/450 |
| 6,270,747 B1 | 8/2001 | Nadel et al. | 424/9.2 |
| 6,346,233 B1 | 2/2002 | Knight et al. | 424/45 |
| 6,375,980 B1 | 4/2002 | Densmore, Jr. et al. | 424/450 |
| 6,440,393 B1 | 8/2002 | Waldrep et al. | 424/45 |
| 6,440,468 B1 | 8/2002 | Quintanilla Almagro et al. | 424/756 |
| 6,462,075 B1 | 10/2002 | Bowen et al. | 514/460 |
| 6,492,333 B1 | 12/2002 | Mundy | 514/18 |
| 6,497,908 B1 | 12/2002 | Oshiro | 426/238 |
| 6,504,048 B1 | 1/2003 | Bachmann et al. | 560/254 |
| 6,566,324 B2 | 5/2003 | Nadel et al. | 514/1 |
| 6,576,273 B2 | 6/2003 | Madsen et al. | 424/756 |
| 6,664,272 B2 | 12/2003 | Snyder et al. | 514/327 |
| 6,673,834 B2 | 1/2004 | Kurz et al. | 514/475 |
| 6,673,843 B2 | 1/2004 | Arbiser | 514/679 |
| 6,998,383 B2 | 2/2006 | Aggarwal et al. | 514/2 |
| 7,030,092 B1* | 4/2006 | Levine | 514/23 |
| 7,105,576 B2 | 9/2006 | Aggarwal | 514/679 |
| 7,196,105 B2* | 3/2007 | Aggarwal | 514/348 |
| 7,371,766 B2 | 5/2008 | Snyder et al. | 514/332 |
| 2001/0025034 A1 | 9/2001 | Arbiser | 514/114 |
| 2001/0036919 A1 | 11/2001 | Nadel et al. | 514/12 |
| 2001/0051184 A1 | 12/2001 | Heng | 424/461 |
| 2002/0006966 A1 | 1/2002 | Arbiser | 514/679 |
| 2002/0019382 A1 | 2/2002 | Snyder et al. | 514/210.2 |
| 2002/0035090 A1 | 3/2002 | Zeldis et al. | 514/58 |
| 2002/0058009 A1 | 5/2002 | Bartus et al. | 424/43 |
| 2002/0058695 A1 | 5/2002 | Majeed et al. | 514/464 |
| 2002/0192274 A1 | 12/2002 | Ponnappa | 424/450 |
| 2003/0021752 A1 | 1/2003 | Whittle et al. | 424/45 |
| 2003/0027830 A1 | 2/2003 | Bowen et al. | 514/252.11 |
| 2003/0096027 A1* | 5/2003 | Babish et al. | 424/756 |
| 2003/0118672 A1 | 6/2003 | McPeak et al. | 424/750 |
| 2003/0149113 A1 | 8/2003 | Caplan et al. | 514/679 |
| 2003/0190381 A1* | 10/2003 | Bland et al. | 424/757 |
| 2004/0058021 A1 | 3/2004 | Aggarwal | 424/756 |
| 2004/0167072 A1 | 8/2004 | Aggarwal et al. | 514/12 |
| 2004/0176384 A1 | 9/2004 | Snyder et al. | 514/252.14 |
| 2005/0049299 A1 | 3/2005 | Aggarwal | 514/456 |
| 2005/0069551 A1 | 3/2005 | Shoji et al. | 424/178.1 |
| 2005/0148599 A1 | 7/2005 | Bowen et al. | 514/255.05 |
| 2005/0181036 A1 | 8/2005 | Aggarwal et al. | 424/450 |

(Continued)

FOREIGN PATENT DOCUMENTS

EP    0317281    5/1989

(Continued)

OTHER PUBLICATIONS

Bharti et al., "Curcumin (diferuloylmethane) down-regulates the constitutive activation of nuclear factor-kB and Ikbalpha kinase in human multiple myeloma cells, leading to suppression of proliferation and induction of apoptosis," *Blood*, 101:1053-1062, 2003.

(Continued)

*Primary Examiner*—Raymond J Henley, III
(74) *Attorney, Agent, or Firm*—Fulbright & Jaworski LLP

(57) ABSTRACT

The present invention provides a method of reducing or inhibiting osteoclast development induced by the receptor for activation of nuclear factor kappa B ligand (RANKL), comprising the step of contacting said osteoclast, or a precursor of the osteoclast, with a pharmacologically effective dose of compounds such as diferuloylmethane, guggulsterone, 1'-Acetoxychavicol or analogues thereof.

16 Claims, 31 Drawing Sheets

U.S. PATENT DOCUMENTS

| | | |
|---|---|---|
| 2005/0201976 A1 | 9/2005 | Aggarwal .................. 424/85.1 |
| 2006/0019907 A1 | 1/2006 | Aggarwal et al. ............. 514/26 |
| 2006/0210656 A1 | 9/2006 | Aggarwal .................. 424/756 |
| 2006/0233899 A1 | 10/2006 | Aggarwal .................. 424/756 |
| 2007/0270464 A1 | 11/2007 | Liotta et al. ................. 514/318 |

FOREIGN PATENT DOCUMENTS

| | | |
|---|---|---|
| EP | 0923941 | 6/1999 |
| WO | WO 00/70949 | 11/2000 |
| WO | WO 01/40188 | 6/2001 |
| WO | WO 03/006033 | 1/2003 |
| WO | WO 03/090681 | 11/2003 |
| WO | WO 2004/091578 | 10/2004 |

OTHER PUBLICATIONS

Bucay et al., "osteoprotegerin-deficient mice develop early onset osteoporosis and arterial calcification," *Genes Dev.*, 12:1260-1268, 1998.

Hsu et al., "Tumor necrosis factor receptor family member RANK mediates osteoclast differentiation and activation induced by osteoprotegerin ligand," *Proc. Natl. Acad. Sci. USA*, 96:3540-3545, 1999.

Kong et al., "OPGL is a key regulator of osteoclastogenesis, lymphocyte development and lymph-node organogenesis," *Nature*, 397:315-323, 1999.

Kumar et al., "Curcumin (Diferuloylmethane) inhibition of tumor necrosis factor (TNF)-mediated adhesion of monocytes to endothelial cells by suppression of cell surface expression of adhesion molecules and of nuclear factor-kappaB activation," *Biochem. Pharmacol.*, 55:775-783 1998.

Lacey et al., "Osteoprotegerin ligand is a cytokine that regulates osteoclast differentiation and activation," *Cell*, 93:165-176, 1998.

Li et al., "RANK is the intrinsic hematopoietic cell surface receptor that controls osteoclastogenesis and regulation of bone mass and calcium metabolism," *Proc Natl. Acad Sci USA*, 97:1566-1571, 2000.

Lomaga et al., "TRAF6 deficiency results in osteopetrosis and defective interleukin-1, CD40, and LPS signaling," *Genes Dev.*, 13:1015-1024, 1999.

Singh and Aggarwal, "Activation of transcription factor NF-kappa B is suppressed by curcumin (diferuloylmethane)," *J. Biol. Chem.*, 270:24995-25000, 1995.

"Analogue," Merriam-Webster's Medical Desk Dictionary, Merriam-Webster, Inc., Springfield, MA, p. 34, 1996.

Ishida et al., "Antitumor agents. Part 214: synthesis and evaluation of curcumin analogues as cytotoxic agents," *Bioorg. Med. Chem.*, 10:3481-3487, 2002.

Khopde et al., "Free radical scavenging ability and antioxidant efficiency of curcumin and its substituted analogue," *Biophys. Chem.*, 80:85-91, 1999.

Kumar et al., "4-Hydroxy-3-methoxybenzoic acid methyl ester: a curcumin derivative targets Akt/NF kappa B cell survival signaling pathway: potential for prostate cancer management," *Neoplasia*, 5:255-266, 2003.

Lin et al., "Inhibition by dietary dibenzoylmethane of mammary gland proliferation, formation of DMBA-DNA adducts in mammary glands, and mammary tumorigenesis in Sencar mice," *Cancer Lett.*, 168:125-132, 2001.

Vajragupta et al., "Manganese complexes of curcumin analogues: evaluation of hydroxyl radical scavenging ability, superoxide dismutase activity and stability towards hydrolysis," *Free Radic. Res.*, 38:303-314, 2004.

Wu et al., "The hypolipidemic natural product guggulsterone acts as an antagonist of the bile acid receptor," *Mol. Endocrinol.*, 16:1590-1597, 2002.

"Turmeric Tales," Food Product Design: Spice Rack, Mar. 2001 www.foodproductDesign.com/archive/2001/0301sr.html.

Aggarwal et al., "Anticancer potential of curcurmin: preclinical and clinical studies," Anticancer Research, 23:363-398, 2003.

Alexanian et al., "High-dose Glucocorticoid Treatment of Resistant Myeloma," *Ann. Int. Med.*, 105:8-11, 1986.

Arbuck et al., "Cancer Therapy Evalutation Program, national Cnacer Institute, Bethesda, Maryland," *Hematology/oncology clinics of North America*, 8(1): 121-140, Medline Abstract AN94201161, 1994, Asai and Miyazawa, "Dietary Curcuminoids prevent high-fat-diet-induced lipid accumulation in rat liver and epididymal adipose tissue," *J. Nutr.*, 131:2932-2935, 2001.

Asai and Miyazawa, "Occurrence of orally administered Curcuminoid as glucuronide and glucuronide/sulfate conjugates in rat plasma," *Life Sci.*, 67:2785-2793, 2000.

Berenson et al., "The role of nuclear factor-kappaB in the biology and treatment of multiple myeloma," *Semin. Oncol.*, 28(6):626-633, 2001.

Bredel, "Anticancer drug resistance in primary human brain tumors," *Brain Red. Brain Res. Rev.*, 35:161-204, 2001.

Brennan and O'Neil, "Inhibition of nuclear factor KappaB by direct modification in whole cells-mechanism of action of nordihydroguaiaritic acid, curcumin and thiol modifiers," *Biochem. Pharmacol.*, 55:965-973, 1998.

Chaturvedi et al., "Assay for redox-sensitive transctiption facotr," *Methods Enzymol.*, 319:585-602, 2000.

Chaturvedi et al., "Tumor necrosis factor and lymphotoxin. Qualitative and quantitative differences in the mediation of early and late cellular response," *J. Biol. Chem.*, 269:14575, 1994.

Cheng et al., "Phase I chemoprevention clinical trial of curcumin," *Proc. Am. Soc. Clin. Oncol.*, 17:558a, 1998.

Estrov et al., "Phenylarsine oxide blocks interleukin-1 beta-induced activation of nuclear transcription factor NF-kappaB, inhibits proliferation, and induces apoptosis od acute myelogenous leukemia cells," *Blood*, 94:2844-2853, 1999.

Feinman et al., "Role of NF-kappaB in the rescue of multiple myeloma cells from glucocorticoid-induced apoptosis in bcl-2,"*Blood*, 93:3044-3052, 1999.

Frankel et al., "Diphtheria fusion protein therapy of chemoresistant malignancies," *Current Cancer Drug Targets*, 2:19-36, 2002.

Glemon et al., "A phase I-II study of bi-weekly paclitaxel as first-line treatment in metastatic breast cancer," *Annals of Oncology*, 9:1247-1249, 1998.

Giri and Aggarwal, "Constitutive activation of NF-kappaB causes resistance to apoptosis in human cutaneous T cell lymphoma HuT-78 cells. Autocrine role of tumor necrosis factor and reactive oxygen intermediates," *J. Biol. Chem.*, 273:14008-14014, 1998.

Golub et al., "Molecular Classification of Cancer: Class Discovery and Class Prediction by Gene Expression Monitoring," *Science*, 286:531-537, 1999.

Han et al., "Curcumin causes the growth arrest and apoptosis of B cell lymphoma by downregulation of egr-1, c-myc, bcl-XL, NF-kappa B, and p53," *Clin. Immunol.*, 93:152-161, 1999.

Helmbach et al., "Drug-resistance in human melanoma," *Int. J. Cancer*, 93:617-622, 2001.

Henke et al., "Comparison of human COP9 signalsome and 26S proteasome 'lid'," *Molecular Biology Reports*, 26:29-34, 1999.

Hour et al., "Curcumin enhances cytotoxicity of chemotherapeutic agents in prostate cancer cells by including p21 (WAF1/CIP1) and C/EBPbeta expressions and suppressing NF-kappaB activation," *Prostate*, 51:211-218, 2002.

Huang et al., "Effect of dietary curcumin and dibenzoylmethane on formation of 7,12-dimethylbenz[a]anthracene-induced mammary tumors and lymphomas/leukemias in Sencar mice," *Carcinogenesis*, 19:1697-1700, 1998.

Ichiki et al., "Regulation of activator protein-1 activity in the mediastinal lymph node metastasis of lung cancer," *Clin. Exp. Metastasis*, 18:539-545, 2001.

Inano et al., "Chemoprevention by Curcumin during the promotion stage of tumorigenesis of mammary gland in rats irradiated with gamma-rays," *Carcinogenesis*, 20:1011-1018, 1999.

Jaffe et al., "Adjuvant methotrexate and citrovorum-factor treatment of osteogenic sarcoma," *N. Engl. J. Med.*, 291:994-997, 1974.

Jang et al., "A curcuminoid and sesquiterpenes as inhibitors of macrophage TNF-alpha release from Curcuma zedoaria," *Planta Med.*, 67:550-552, 2001.

Janson, "Letter from Dr. Janson," 2001 Newsletter, pp. 1-7, www.drjanson.com/djhl-html/2001/news-2001-12.htm.

Jaruga et al., "Apoptosis-like, reversible changes in plasma membrane asymmetry and permeability, and transient modifications in mitochondrial membrane potential induced by curcumin in rat thymocytes," *FEBS Lett.*, 433:287-293, 1998.

Jobin et al., "Curcumin blocks cytokine-mediated NF-kappa B Activation and proinflammatory gene expression by inhibiting inhibitory factor I-kappa B kinase activity," *J. Immunol.*, 163:3474-3483, 1999.

Kamat et al., "Curcumin potentiates the appoptotic effects of chemotherapeutic agents and cytokines through down-regulation of nuclear factor-kappaB and nuclear factor-kappaB-regulated gene products in IFN-alpha-sensitive and IFN-alpha-resistant human bladder cancer cells," *Mol Cancer Ther.*, (3): 1022-1030, 2007.

Kawamorti et al., "Chemopreventive effect of curcumin, a naturally occuring anti-inflammatory agent, during the promotion/progression stages of colon cancer," *Cancer Res.*, 59:597-601, 1999.

Knight et al ed., Viral and Mycolplasmal Infections or the Respiratory Tract, p. 7 1973.

Knight et al., "Anticancer exffect of 9-nitrocamptothecin liposome aerosol on human cancer xenografts in nude mice," *Cancer Chemother Pharmacol*, 44:177-186, 1999.

Koshkina et al., "Cyclosporin A aerosol improves the anticancer effect of paclitaxel aerosol in mice," *Journal of Aerosol Medicine*, 17(1):7-14, 2004.

Koshkina et al., "Distribution camptothecin after delivery as a liposome aerosol of following intramuscular injection in mice," *Cancer chemother Pharmacol*, 44:187-193, 1999.

Koshkina et al., "Improved respiratory delivery of the anticancer drugs, camptothecin and paclitaxel, with 5% CO2-enriched air: pharmacokinetic studies," *Cancer Chemother Pharmacol*, 47:451-456, 2001.

Kunnumakkara et al., "Curcumin potentiates antitumor activity of gemcitabine in an orthotopic model of pancreatic cancer through suppression of proliferation, antiogensis, and in inhibition of nuclear factor-kappaB-regulated gene products," *Cancer Res.*, (8): 3853-3861, 2007.

Kuttan et al., "Potential anticancer activity of tumeric (curcuma longa)," *Cancer Letters*, 29:197-202, 1985.

Letsou et al., "Pharmacokinetics of liposomal aerosolized cyclosporine A for pulmonary immunosuppression," *Ann Thorac Surg*, 68:2044-2048, 1999.

Lin et al., "Curcumin inhibits tumor growth and angiogenesis in ovarian carcinoma by targeting the nuclear factor-kappaB pathway," *Clin Cancer Res.*, 11: 3423-3430, 2007.

Liposomes: A Practical Approach, R.R.C. New ed., Oxford University Press, 1990.

Manna and Aggarwal, "Lipopolysaccharide inhibits TNF-induced apoptosis: role of nuclear factor-kappaB activation and reactive intermediates," *J. Immunol.*, 162:1510-1518, 1999.

Manna et al., "Leflunomide suppresses TNF-induced cellular responses: effects on NF-kappa B, activator protein-1, c-Jun N-terminal protein kinase, and apoptosis," *J. Immunol.*, 165:5962-5969, 2000.

Manna et al., "Overexpression of manganese superoxide dismutase suppresses tumor necrosis factor-induced apoptosis and activation of nuclear transcription factor-kappaB and Activated protein-1," *J. Biol. Chem.*, 273:13245-13254, 1998.

Mehta et al., "Antiproliferative effect of curcumin (diferuloymethane) against human breast tumor cell lines," *Anti-Cancer Drugs*, 8:470-481, 1997.

enon et al., "Anti-metastatic activity of curcumin and catechin," *Cancer Lett.*, 141:159-165, 1999.

Miller et al., "Taxanes in the treatment of breast cancer: a prodigy comes of age," *Cancer Invest.*, 17:121-136, 1999 (PubMed Abstract).

Mohan et al., "Curcuminoids inhibit the angiogenic response stimulated by fibroblast growth factor-2, including expression of matrix metalloproteinase gelatinase B," *J. Biol. Chem.*, 275:10405-10412, 2000.

Ni et al., "Analysis of expression of nuclear factor kappa B (NF-kappa B) in multiple myeloma: downregulation of NF-kappa B includes apoptosis," *Br. J. Haematol.*, 115:279-286, 2001.

Pahl et al., "Activators and target genes of Rel/NF-kappaB transcription factors," *Oncogene*, 18:6853-6866, 1999.

Pan et al., "Comparative studies on the suppression of nitric oxide synthase by curcumin and its hydrogenated metabolites through down-regulation of IkappaB kinase and NFkappaB activation in macrophages," *Biochem. Pharmacol.*, 60:1665-1676, 2000.

Pervaiz et al., "Antitumor and antiviral activity of curcumin and light," *Proc. Am. Assoc. Cancer Res.*, 31:392, 1990.

Piwocka et al., "Curcumin induces caspase-3-independent apoptosis in humna multidrug-resistant cells," *Annal of the New York Academy of Sciences*, 973:250-254, 2002.

Plummer et al., "Inhibition of cyclo-oxygenase 2 expression in colon cells by the chemopreventive agent curcumin involves inhibition of NF-kappaB activation via the NIK/IKK signaling complex," *Oncogene*, 18:6013-6020, 1999.

Podar et al., "Essential role of caveolae in interleukin-6- and insulin-llike growth factor I-triggered Akt-1-mediated survival of multiple myeloma cells," *J. Biol. Chem.*, 278:5794-5801, 2002.

Poland et al., "Study of therapy resistance in cancer cells with functional proteome analysis," *Clin. Chem. Lab. Med.*, 40:221-234, 2002.

Ramachandran et al., "Differential sensitivity of human mammary epithelial and breast carcinoma cell lines to curcumin," *Breast Cancer Res. And Treat.*, 54:269-278, 1999.

Ramprasad and Sirsi, *Indian medicianl plants: Curcuma longa-effect of curcumin and the essential oils of C. Longa on bile secretion*, *J. Sci. Ind. Res.*, 15C:262-265, 1956 (Abstract from Database CAPLUS, Database Accession Number 1957:68566).

Rao et al., "Chemoprevention of colon carcinogensis by dietary curcumin, a naturally occuring plant phenolic compound," *Cancer Res.*, 55:259-266, 1995.

Serrone and Hersey, "The Chemoresistance of human malignant melanoma: an update," *Melanoma Res.*, 9:51-58, 1999.

Shishodia and Aggarwal, "Nuclear factor-kappaB activation: a question of life or death," *J. Biochem. Mol. Biol.*, 35:28-40, 2002.

Shishodia et al., "Curcumin (diferuloylmethane) down-regulates cigarette smoke-induced NF-kB activation through inhibition of IkBα kinase in human lung epithelial cells: correlation with suppression of COX-2, MMP-9 and cyclin D1," *Carcinogensis*, 24(7):1269-1279, 2003.

Simon et al., "Inhibitory effect of curcuminoids on MCF-7 cell proliferation and structure-activity relationships," *Cancer Lett.*, 129:111-116, 1998.

Singletary et al., "Inhibition of 7,12-dimethylbenz[a]anthracene (DMBA)-induced mammary tumorigenesis and DMBA-DNA adduct formation by curcumin," *Cancer Lett.*, 103:137-141, 1996.

Sonneveld et al., "Cyclosporin A combined with vincristine, doxorubicin and dexamethasone (VAD) compared with VAD alone in patients with advnaced refactory multiple myeloma: an EORTC-HOVON randomized phase III study (06914)," *Br. J. Haematol.*, 115:895-902, 2001.

Sriganth et al., "Dietary curcumin with cisplatin administration modulates tumor marker indices in experimental fibrosarcoma," *Pharmacological Res.*, 39:175-179, 1999.

Supplementary European Search Report, issued in European Patent Application No. 03718509.1, dated Nov. 8, 2007.

Verschraegen et al., "Clinical evaluation of the delivery and safety of aeroslolized liposomal 9-nitro-20(S)-camptothecin in patients with advanced pulmonary malignancies," *Clinical Cancer Research*, 10:2319-2326, 2004.

Voskoglou-Nomikos et al., "Clinical predictive value of the in vitro cell line, human xenograft, and mouse allograft preclinical cancer models," *Clin. Cancer Res.*, 9:4227-4239, 2003.

Waldrep et al., "High dose cyclosporin A and budesonide-liposome aerosols," *International Journal of Pharmaceuticals*, 152:27-36, 1997.

Waldrep et al., "Nebulized glucocorticoids in liposomes: aerosol characteristics and human dose estimates," *Journal of Aerosol Medicine*, 7(2):135-145, 1994.

Waldrep et al., "Operating characteristics of 18 different continuous-flow jet nebulizers with beclomethasone dipropionate liposome aerosol," *Chest*, 105:106-110, 1994.

Wang et al., "TNF- and Cancer Therapy-Induced Apoptosis: Potentiation by Inhibition of NF-kappaB." *Science*, 274:784-787, 1996.

Westerheide et al., "The putative oncoprotein Bcl-3 induces cyclin D1 to stimulate G(1) transition," *Mol. Cell. Biol.*, 21:8428-8436, 2001.

Zhang et al., "Curcumin inhibits cyclooxygenase-2 transcription in bile acid- and phorbol ester-treated human gastrointestinal epithelial cells," *Carcinogensis*, 20:445-451, 1999.

Zhang et al., "Effects of curcumin in combination with adriamycin in KB and KBv200 cells," *Zhongguo Yaolixue Tongbao*, 17:702-704, 2001.

Zhang et al., "Tyrosine kinase inhibitor emodin suppresses gowth of HER-2/neu-overexpressing breast cancer cells in athymic mice and sensitizes these cells to the inhibitory effect of paclitaxel," *Clin. Cancer Res.*, 5:343-353, 1999.

\* cited by examiner

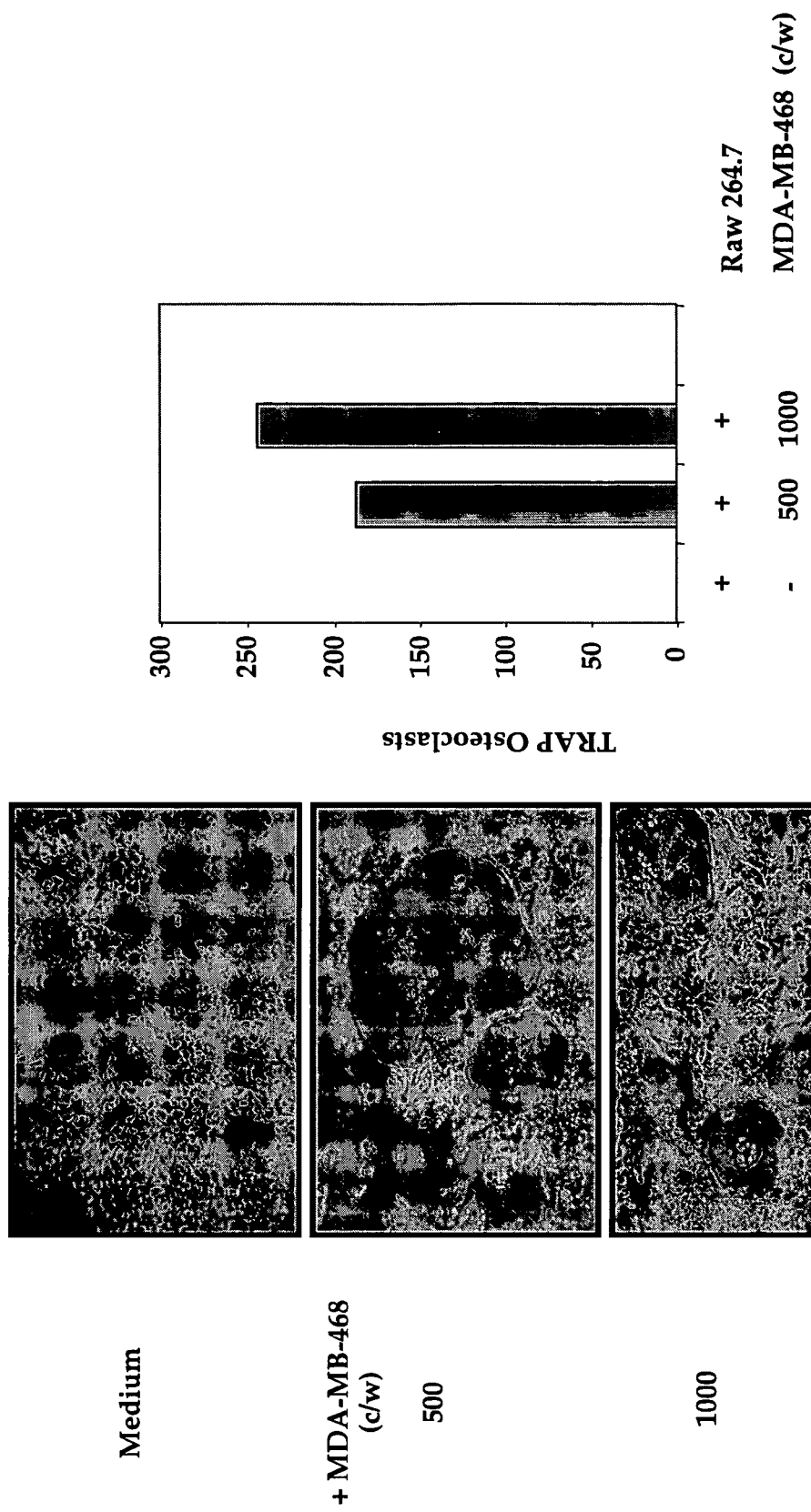

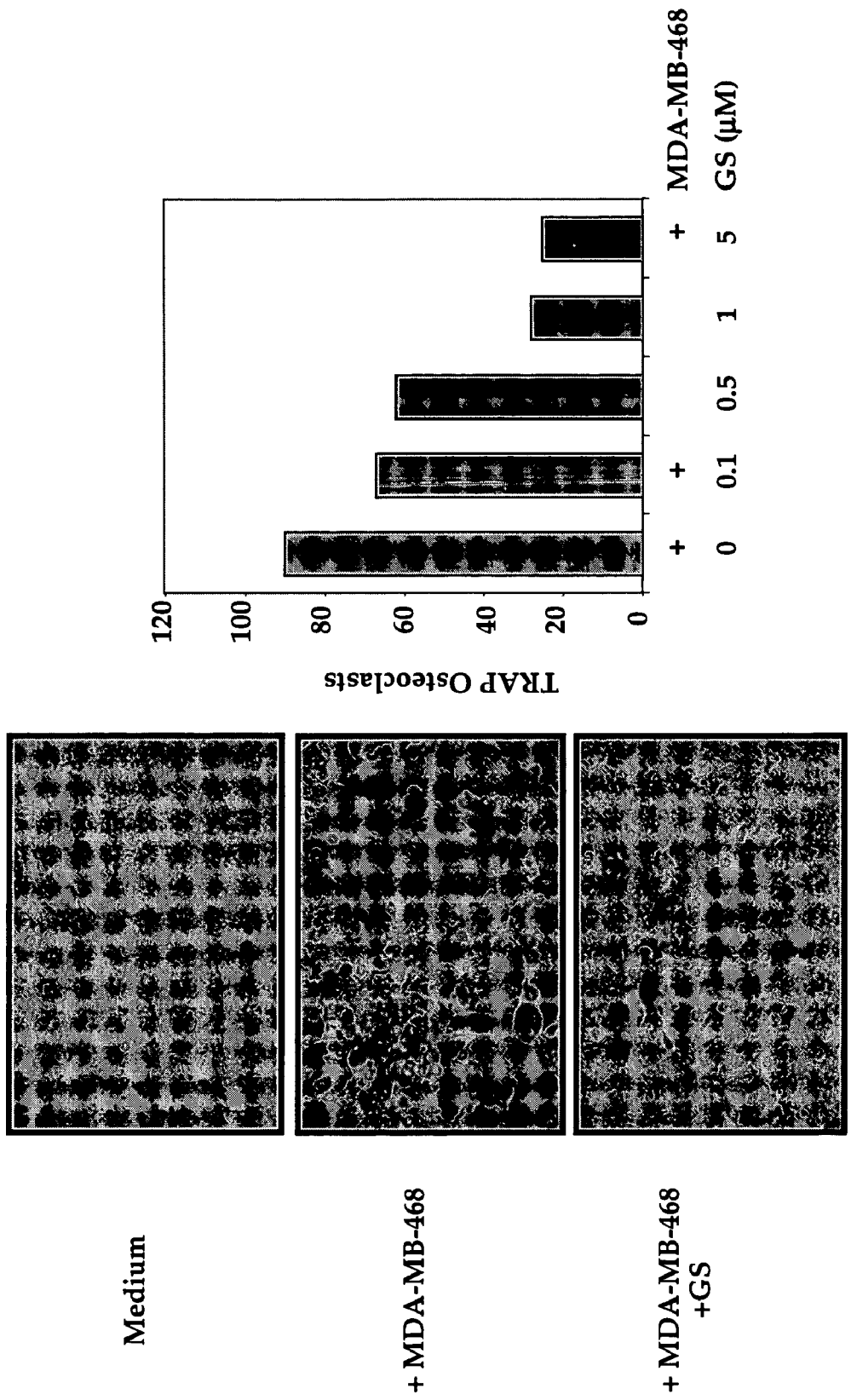

OSTEOCLASTOGENESIS INHIBITORS AND USES THEREOF

CROSS-REFERENCE TO RELATED APPLICATION

This patent application claims benefit of priority of provisional patent application U.S. Ser. No. 60/497,841, filed Aug. 26, 2003, now abandoned.

FEDERAL FUNDING LEGEND

This invention was produced in part using funds obtained through a Department of Defense US Army Breast Cancer Research Program grant (BC010610), a PO1 grant (CA91844) from the National Institutes of Health and a P50 Head and Neck SPORE grant from the National Institutes of Health. Consequently, the federal government has certain rights in this invention.

BACKGROUND OF THE INVENTION

1. Field of the Invention

The present invention relates generally to the molecular biology of osteoclastogenesis. More specifically, the present invention relates to inhibitors of osteoclastogenesis and uses thereof.

2. Description of the Related Art

Nuclear Factor-kB (NF-kB) represents a group of five proteins, namely c-Rel, Rel A (p65), Rel B, NF-kB1 (p50 and p105), and NF-kB2 (p52). NF-kB is regulated by a family of inhibitors called IkB. In an inactive state, NF-kB is present in the cytoplasm as a heterotrimer consisting of p50, p65, and IkBa subunits. In response to an activation signal, the IkBa subunit is phosphorylated at serine residues 32 and 36, ubiquitinated at lysine residues 21 and 22, and degraded through the proteosomal pathway, thus exposing the nuclear localization signals on the p50-p65 heterodimer. The p65 is then phosphorylated, leading to nuclear translocation and binding to specific DNA sequence, which in turns results in gene transcription.

The p65 subunit of NF-kB, which contains at least two strong transactivation domains (TAD) within the C terminus (TA1 30 amino acid; TA2 90 amino acid), has been shown to undergo phosphorylation upon activation. The sites of phosphorylation and the kinase responsible for p65 phosphorylation remain controversial. For instance, phosphorylation at Ser 276 by protein kinase A, at Ser 529 by casein kinase II, at Ser 536 by IKK-b, and at serine 471 by PKC-e have been demonstrated. In addition, phosphorylation of p65-TAD by glycogen synthase kinase-3b and by $Ca^{2+}$/calmodulin-dependent protein kinase IV have been demonstrated.

NF-kB has been shown to regulate the expression of a number of genes whose products are involved in inflammation, viral replication, carcinogenesis, anti-apoptosis, invasion and metastasis. These include anti-apoptosis genes, adhesion molecules, chemokines, inflammatory cytokines, and cell cycle regulatory genes. Thus agents that can suppress NF-kB activation have the potential to treat a variety of diseases that involves inflammation, apoptosis and carcinogenesis (Garg and Aggarwal, 2002; Karin and Lin, 2002; Zingarelli et al., 2003; Rosak et al., 2002).

Osteoclasts are multinucleated cells formed by the fusion of mononuclear progenitors of the monocyte/macrophage family and are the major resorptive cell of bone (Teitelbaum, 2000). In vitro maturation of macrophages into osteoclasts requires the presence of stromal cells or their osteoblast progeny (Udagawa et al., 1990). Extensive research in the last few years has indicated that these accessory cells express macrophage colony stimulating factor (MCSF) and receptor for activation of nuclear factor kappa B (NF-κB) (RANK) ligand (RANKL) and these are essential and sufficient to promote osteoclastogenesis. Besides macrophage colony stimulating factor and RANKL, several other inflammatory cytokines including TNF and IL-1β have been implicated in osteoclastogenesis, most likely through the osteoblastic modulation of RANKL and mCSF, respectively. The effects of parathyroid hormone and lipopolysaccharides on osteoclastogenesis are also mediated through expression of RANKL.

RANKL is a member of the TNF superfamily (Darnay & Aggarwal, 1999) that interacts with the cells surface receptor RANK, which in turn recruits TNF receptor-associated factors (TRAF)-1, 2, 3, 5 and 6 (Darnay et al., 1998; Wong et al., 1998). By receptor deletion analysis, sequential recruitment of TRAF6 and NF-κB-inducing kinase (NIK) by RANK was shown to lead to NF-κB activation, and recruitment of TRAF2 leads to JNK activation (Darnay et al., 1999; Lee et al., 1997).

That RANK can mediate osteoclastogenesis was first demonstrated by Hsu et al (Hsu et al., 1999). Further gene-deletion analysis of RANK, RANKL, and TRAF6 showed that these genes are positive regulators of osteoclastogenesis (Kong et al., 1999; Li et al., 2000; Lomaga et al., 1999), whereas osteoprotegerin (OPG), a decoy receptor for RANKL, was found to be a negative regulator of this process (Bucay et al., 1998; Lacey et al., 1998). Gene-deletion analysis also suggested a critical role of macrophage colony stimulating factor, c-fms (macrophage colony stimulating factor receptor) and Src in osteoclastogenesis (Dai et al., 2002; Tiffee et al., 1999; Xing et al., 2001).

Although RANKL is known to activate NF-κB, JNK, p42/p44 MAPK, and p38 MAPK (Darnay et al., 1999; Lee et al., 1997; Matsumoto et al., 2000; Zhang et al., 2001), how this cytokine mediates osteoclastogenesis is not fully understood. Furthermore agents that can suppress RANKL signaling can suppress osteoclastogenesis-induced bone loss. Because curcumin has been shown to suppress NF-κB activation induced by various inflammatory stimuli (Kumar et al., 1998, Bharti, 2003 #4; Singh & Aggarwal, 1995), inhibit the activation of IKK needed for NF-κB activation (Jobin et al., 1999; Pan et al., 2000; Plummer et al., 1999), and, found to be safe in humans even at 8 g per day (Cheng et al., 2001), the effect of curcumin on RANKL-induced NF-κB activation and on osteoclastogenesis in osteoclast precursor cells was examined.

The prior art is deficient in the demonstration that RANKL induces NF-κB activation through activation of IκB kinase (IKK), and IκBα phosphorylation and degradation and curcumin inhibits RANKL-induced NF-κB activation and osteoclastogenesis. The present invention fulfills this long-standing need and desire in the art.

SUMMARY OF THE INVENTION

Numerous studies have indicated that inflammatory cytokines play a major role in osteoclastogenesis, leading to bone resorption that is frequently associated with cancers and other diseases. Gene deletion studies have shown that receptor activation of NF-κB ligand (RANKL) is one of the critical mediators of osteoclastogenesis. How RANKL mediates osteoclastogenesis is not fully understood, but an agent that suppresses RANKL signaling has potential to inhibit osteoclastogenesis. The present invention demonstrated the ability of curcumin (diferuloylmethane), a pigment derived from turmeric, to suppress RANKL signaling and osteoclastogenesis in RAW264.7 cells, a murine monocytic cell line. Treatment of these cells with RANKL activated NF-κB, and pre-exposure of the cells to curcumin completely suppressed RANKL-induced NF-κB activation. Curcumin inhibited the pathway leading from activation of IκBα kinase and IκBα phosphorylation, to IκBα degradation. RANKL induced osteoclastogenesis in these monocytic cells, and curcumin inhibited RANKL-induced osteoclastogenesis. Curcumin suppressed osteoclastogenesis maximally when added together with RANKL, and minimally when it was added 2 days after RANKL. Whether curcumin inhibits RANKL-induced osteoclastogenesis through suppression of NF-κB was also confirmed independently, as RANKL failed to activate NF-κB in cells stably transfected with dominant-negative form of IκBα and concurrently failed to induce osteoclastogenesis. Thus overall these results indicate that RANKL induces osteoclastogenesis through the activation of NF-κB and treatment with curcumin inhibits both the NF-κB activation and osteoclastogenesis induced by RANKL.

Additionally, the present invention also demonstrated that guggulsterone and 1'-Acetoxychavicol suppressed RANKL-induced osteoclastogenesis through suppression of NF-κB. The present invention also demonstrates that pre-treatment of cells with either guggulsterone or 1'-Acetoxychavicol suppressed RANKL-induced NF-κB activation. The present invention further demonstrated the ability of guggulsterone to suppress RANKL-induced IKK activation and the ability of 1'-Acetoxychavicol to suppress RANKL-induced IκBα degradation and phosphorylation. Additionally, both guggulsterone and 1'-Acetoxychavicol suppressed RANKL-induced osteoclastogenesis only when added together.

Further, the present invention also demonstrated the ability of tumor cells such as head and neck squamous cell carcinoma and breast adenocarcinoma to induce osteoclastogenesis through expression of RANKL. Both guggulsterone and 1'-Acetoxychavicol suppressed osteoclastogenesis induced by breast adenocarcinoma cells. Additionally the present invention also demonstrated the expression of both RANK and RANKL on the surface on MCF-7 cells. These findings indicate that tumor cells induced osteoclastogenesis through expression of RANKL, which was suppressed by both 1'-Acetoxychavicol and guggulsterone.

In one embodiment, the present invention provides a method of reducing or inhibiting osteoclast development induced by the receptor for activation of nuclear factor kappa B ligand (RANKL), comprising the step of contacting the osteoclast, or a precursor of the osteoclast, with a pharmacologically effective dose of compounds comprising diferuloylmethane, guggulsterone, 1'-Acetoxychavicol or analogues thereof.

In another embodiment, the present invention provides a method of inhibiting the formation of osteoclasts in an individual in need of such treatment, comprising the step of administering to the individual a pharmacologically effective dose of compounds comprising diferuloylmethane, guggulsterone, 1'-Acetoxychavicol or analogues thereof.

In yet another embodiment, the present invention provides a method of reducing osteolytic activity and bone loss in an individual in need of such treatment, comprising the step of administering to the individual a pharmacologically effective dose of compounds comprising diferuloylmethane, guggulsterone, 1'-Acetoxychavicol or analogues thereof.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 1A shows the effect of curcumin on RANKL induced NF-κB activation in RAW 264.7 cells ($1 \times 10^6$ cells) that were either incubated alone or in the presence of curcumin (50 μM) for 2 hours and then treated with RANKL (10 nM) for the indicated times.

FIG. 1B shows the effect of varying concentrations of curcumin on RANKL induced NF-κB activation in RAW 264.7 cells ($1 \times 10^6$ cells) that were incubated without or with the indicated concentrations of curcumin for 2 h and then treated with RANKL (10 nM) and tested for nuclear NF-κB by EMSA as described.

FIG. 2A compares the level of IκBα; FIG. 2B compares the level of phosphorylated IκBα by Western blotting; FIG. 2C compares the IKK activity (upper panel: immunoprecipitated IKK and performed the kinase assay) and total IKKα and IKKβ proteins using Western blotting (middle and lower panels) in cytoplasmic extracts.

FIG. 3A shows that TRAP$^+$ cells were photographed (original magnification, 100×), and FIG. 3B shows that multinucleated (>3 nuclei) osteoclasts were counted (error bar indicates s.d.).

FIG. 4A shows photographs of cells (original magnification, 100×). FIG. 4B shows multinucleated (>3 nuclei) osteoclasts were counted. Values indicate mean of total osteoclasts in triplicate cultures (error bar indicates s.d.).

FIG. 5A shows that $1 \times 10^6$ cells were incubated alone or in the presence of RANKL (10 nM) or TNF (1 nM) for 30 minutes and tested for nuclear NF-κB by EMSA as described. FIG. 5B shows that $1 \times 10^4$ cells were treated in the absence or presence of RANKL (5 nM) for 5 days, TRAP-stained and examined for osteoclastogenesis.

FIG. 6A shows the effect of guggulsterone on RANKL-induced NF-κB activation. RAW264.7 cells ($1 \times 10^6$ cells) were incubated with variable concentrations of guggulsterone for 4 h followed by treatment of the cells with RANKL (10 nM) for 25 min. The samples were then analyzed for NF-κB by EMSA. FIG. 6B shows the effect of guggulsterone on RANKL-induced IKK activation. RAW264.7 cells ($5 \times 10^6$ cells) were incubated with guggulsterone (50 μM) for 4 h followed by treatment of the cells with RANKL (10 nM) for different times. The samples were then analyzed for IKK by immune complex kinase assay.

FIG. 7A shows photographs of the cells. FIG. 7B shows the effect of guggulsterone on RANKL-induced TRAP positive cells.

FIG. 8A shows photographs of the cells. FIG. 8B shows the effect of guggulsterone on RANKL-induced TRAP positive cells.

FIG. 9A shows the effect of 1'-Acetoxychavicol on RANKL-induced NF-κB activation at different times. RAW264.7 cells ($1 \times 10^6$ cells) were incubated with 1'-Acetoxychavicol (50 μM) and RANKL (10 nm) for different times. The samples were then analyzed for NF-κB by EMSA. FIG. 9B shows the effect of varying concentrations of 1'-Acetoxychavicol on RANKL-induced NF-κB activation. RAW264.7 cells ($1 \times 10^6$ cells) were incubated with variable concentrations of 1'-Acetoxychavicol and RANKL (10 nM) for 25 min. The samples were then analyzed for NF-κB by EMSA.

FIG. 10A shows the effect of 1'-Acetoxychavicol on RANKL-induced IκBα degradation. RAW264.7 cells ($1 \times 10^6$ cells) were incubated with 1'-Acetoxychavicol (50 μM) and RANKL (10 nM) for different times. The samples were then analyzed for IκBα by western blot. FIG. 10B shows the effect of 1'-Acetoxychavicol on RANKL-induced phosphorylation of IκBα. RAW264.7 cells ($1 \times 10^6$ cells) were incubated with different combinations of 1'-Acetoxychavicol (50 μM), RANKL (10 nM), acetyl-leucyl-leucyl-norleucinal (ALLN, 50 μg/ml) for 25 min. The samples were analyzed for phosphorylated IκBα by western blot.

FIG. 11A shows photographs of the cells. FIG. 11B shows the effect of 1'-Acetoxychavicol on RANKL-induced TRAP positive cells. Numbers on top of the bar indicates cell viability.

FIG. 12A shows photographs of the cells. FIG. 12B shows the effect of 1'-Acetoxychavicol on RANKL-induced TRAP positive cells.

FIG. 13A shows the photograph of cells incubated with different number of HN5 cells. FIG. 13B shows the number of TRAP positive cells in these samples. FIGS. 13C shows the photograph of cells incubated with different number of Fadu cells. FIG. 13D shows the number of TRAP positive cells in these samples.

FIGS. 14A-F show that Breast adenocarcinoma cells induce osteoclastogenesis. RAW264.7 cells ($1 \times 10^4$ cells) were incubated with different numbers of MDA-MB-468 cells or MCF-7 cells or MDA-MB-LV cells for five days. Osteoclastogenesis was then analyzed in these samples by TRAP assay. FIG. 14A show photograph of cells incubated with different numbers of MDA-MB-468 cells. FIG. 14B shows the number of TRAP positive cells in these samples FIG. 14C shows the photograph of cells incubated with different numbers of MCF-7 cells. FIG. 14D shows the number of TRAP positive cells in these samples. FIG. 14E shows photographs of cells incubated different number of MDA-MB-LV cells. FIG. 14F shows the number of TRAP-positive cells in these samples.

FIG. 15A shows photographs of the cells incubated with MDA-MB-468 cells under different conditions. FIG. 15B shows the number of TRAP positive cells in the samples incubated with MDA-MB-468 cells and varying concentrations of 1'-Acetoxychavicol. FIG. 15C shows the photographs of the cells incubated with MCF-7 cells under different conditions. FIG. 15D shows the number of TRAP positive cells in the samples incubated with MCF-7 cells and varying concentrations of 1'-Acetoxychavicol.

FIGS. 16A-D show that guggulsterone suppresses breast adenocarcinoma cells-induced osteoclastogenesis. RAW264.7 cells ($1 \times 10^4$ cells) were incubated with MDA-MB-468 cells ($1 \times 10^3$ cells) or with MCF-7 cells ($1 \times 10^3$ cells) in the presence of varying concentrations of guggulsterone for five days and then analyzed for osteoclastogenesis by TRAP assay. FIG. 16A shows photographs of cells incubated with MDA-MB-468 cells under different conditions. FIG. 16B shows number of TRAP-positive cells in the samples incubated with MDA-MB-468 cells and varying concentrations of guggulsterone. FIG. 16C shows photographs of cells incubated with MCF-7 cells under different conditions. FIG. 16D shows number of TRAP-positive cells in the samples incubated with MCF-7 cells and varying concentrations of guggulsterone.

DETAILED DESCRIPTION OF THE INVENTION

Figure 1A:
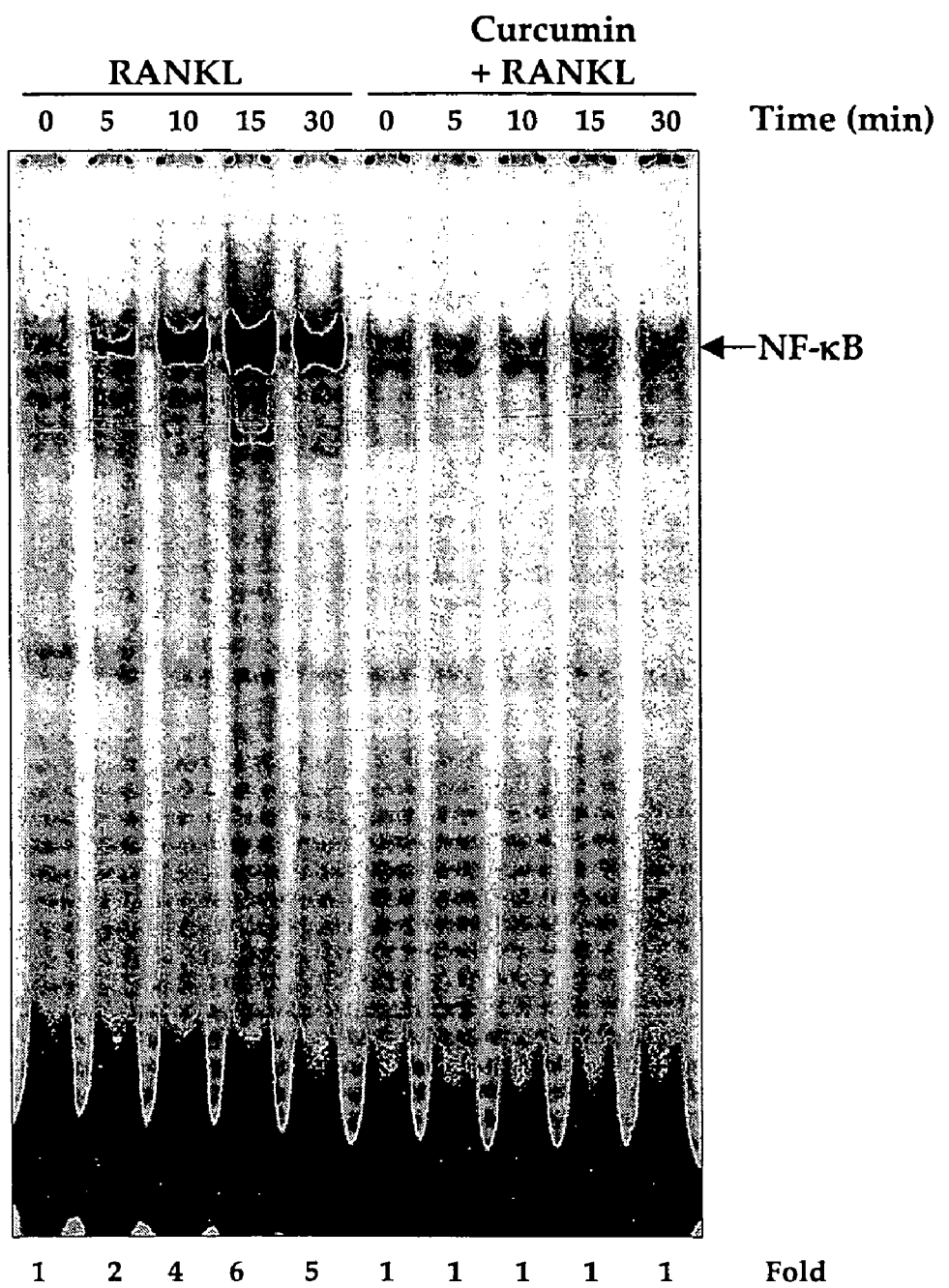
FIGS. 1A-B show that RANKL induces NF-κB activation and curcumin inhibits it in dose- and time-dependent manner.

The following abbreviations may be used herein: NF-κB, nuclear factor-κB; RANKL, receptor activator of nuclear factor-κB ligand; MCSF, macrophage colony-stimulating factor; OPG, osteoprotegerin; IL, interleukin; IFN, interferon; TRAF, TNF receptor-associated factor; IKK, IκB kinase; TRAP, tartrate resistance acid phosphatase; IκBα-DN, dominant negative IκBα mutant; EMSA, electrophoretic mobility gel shift assay; JNK, c-Jun N-terminal kinase; FBS, fetal bovine serum; HRP, horse radish peroxidase; GS, guggulsterone; 1'-Acetoxychavicol (1'-Acetoxychavicol).

The nuclear transcription factor NF-kB has been shown to mediate inflammation, viral replication, carcinogenesis, anti-apoptosis, invasion and metastasis. Thus, specific inhibitors of this factor have therapeutic potential.

The present invention is directed to a method of reducing or inhibiting osteoclast development induced by the receptor for activation of nuclear factor kappa B ligand (RANKL), comprising the step of contacting the osteoclast, or a precursor of the osteoclast, with a pharmacologically effective dose of compounds comprising diferuloylmethane, guggulsterone, 1'-Acetoxychavicol or analogues thereof. In one aspect, the compounds inhibits RANKL-mediated NF-κB activation. Preferably, this inhibition of RANKL-mediated NF-κB activation is by inhibition of IκB kinase activity. To perform this method of the present invention, it is expected that a person having ordinary skill in this art would readily be able to determine the optimal dosage and route of administration of the compounds, for example, in the general diferuloylmethane is in concentration range of from about 0.01 mM to about 1000 mM; guggulsterone is in concentration range of from about 0.01 mM to about 1000 mM; 1'-Acetoxychavicol is in concentration range of from about 0.01 mM to about 1000 mm.

The present invention is further directed to a method of inhibiting the formation of osteoclasts in an individual in need of such treatment, comprising the step of administering to the individual a pharmacologically effective dose of compounds comprising diferuloylmethane, guggulsterone, 1'-Acetoxychavicol or analogues thereof. In one aspect, the compounds inhibit RANKL-mediated NF-κB activation. Additionally, the inhibition of RANKL-mediated NF-κB activation is by inhibition of IκB kinase activity. Preferably, the diferuloylmethane is administered in a concentration of from about 0.01 mg/kg of said individual's body weight to about 100 mg/kg of said individual's body weight; guggulsterone is administered in a concentration of from about 0.01 mg/kg of said individual's body weight to about 100 mg/kg of said individual's body weight; 1'-Acetoxychavicol is administered in a concentration of from about 0.01 mg/kg of said individual's body weight to about 100 mg/kg of said individual's body weight.

The present invention is further directed to a method of reducing osteolytic activity and bone loss in an individual in need of such treatment, comprising the step of administering to said individual a pharmacologically effective dose of compounds comprising diferuloylmethane, guggulsterone, 1'-Acetoxychavicol or analogues thereof. Preferably, the diferuloylmethane is administered in a concentration of from about 0.01 mg/kg of said individual's body weight to about 100 mg/kg of said individual's body weight; guggulsterone is administered in a concentration of from about 0.01 mg/kg of said individual's body weight to about 100 mg/kg of said individual's body weight of said individual's body weight; 1'-Acetoxychavicol is administered in a concentration of from about 0.01 mg/kg of said individual's body weight to about 100 mg/kg of said individual's body weight.

It is expected that the methods described by the present invention would be useful in reducing osteolytic activity and bone loss in an individual suffering from one of a variety of diseases, including but not limited to, breast cancer, multiple myeloma, osteoporosis, e.g., post-menopausal osteoporosis, Paget's disease, rheumatoid arthritis and head and neck squamous cell carcinoma.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Materials

The rabbit polyclonal antibodies to IκBα, p50, p65, cyclin D1, were purchased from Santa Cruz Biotechnology (Santa Cruz, Calif.). Antibodies against phospho-IκBα, and the polynucleotide kinase kit were purchased from Cell Signaling Technology (Beverly, Mass.). Anti-IKKα and anti-IKKβ antibodies were kindly provided by Imgenex (San Diego, Calif.). Goat anti-rabbit-horse radish peroxidase (HRP) conjugate was purchased from Bio-Rad Laboratories (Hercules, Calif.), goat anti-mouse-HRP from Transduction Laboratories (Lexington, Ky.), and MTT from Sigma-Aldrich Chemicals. Curcumin with a purity greater than 98% was purchased from LKT laboratories, Inc. (St. Paul, Minn.) and was prepared as a 20 mM solution in dimethyl sulfoxide and then further diluted in cell culture medium. DMEM-F12, fetal bovine serum (FBS), 0.4% trypan blue vital stain, and anti-biotic-antimycotic mixture were obtained from Life Technologies, Inc. (Grand Island, N.Y.). Protein A/G-Sepharose beads were obtained from Pierce (Rockford, Ill.). [$\gamma^{32}$P]ATP was from ICN Pharmaceuticals (Costa Mesa, Calif.).

EXAMPLE 2

Cells

The mouse macrophage cell line RAW 264.7 was obtained from American Type culture collection. RAW 264.7 cells were cultured in DMEM-F12 medium supplemented with 10% fetal bovine serum and antibiotics. This cell line has been shown to express RANK and differentiate into tartrate resistance acid phosphatase (TRAP)-positive, functional osteoclasts when co-cultured with bone slices or soluble RANKL (Hsu et al., 1999). Moreover, RANKL has been shown to activate NF-κB in these cells (Wei et al., 2001). TRAP staining was performed using a leukocyte acid phosphatase kit (387-A) from Sigma (St. Louis, Mo.).

EXAMPLE 3

Plasmids

The plasmid pCMV4-Flag-IκBα-DN (lacking residues 1-36) was provided by Dr. Dean W. Ballard (Vanderbilt University School of Medicine, Nashwille, Tenn.) (Brockman et al., 1995; Singh et al., 1996). The tetracycline inducible expression vector pEC 1214A was provided by Dr. Hong-Ji-Xu (The University of Texas M. D. Anderson Cancer Center, Houston, Tex.) (Haridas et al., 1998). A tetracycline inducible FLAG-tagged IκBα-DN was constructed by inserting a Hindlll-BamHl fragment from pCW4-Flag-IκBα-DN into the Hindlll-BamHl site of pEC 1214A, and the resulting plasmid was named pTet-Flag-IκBα-DN. The expression vector of full-length murine RANKL (pcDNA3.I-TRANCE) was provided by Yongwon Choi (Rockefeller University, New York, N.Y.).

To generate a bacterial expression vector for RANKL, specific 5' and 3' primers with Hindlll and Notl sites were used, respectively, to amplify the DNA, which encodes residues 157-316 of RANKL from the pcDNA3-TRANCE template. The PCR product was digested with Hindlll-Notl and ligated in-frame with an HA-tag (N terminal) and a histidine tag (C-terminal) into the expression vector pHB6. Soluble RANKL was expressed and purified using Ni-agarose.

EXAMPLE 4

RAW264.7 Cells Stably Expressing Flag-IκBα-DN

RAW264.7 cells were plated at 0.5×10⁶ cells/well on 6-well plates and transfected the next day with pTet-Flag-IκBα-DN (2.5 μg total DNA) using 9 μl of Fugene. After 48 hours, cells were trypsinized and plated in 100-cm dishes in the presence of G418 (600 μg/ml) and tetracycline (1 μg/ml). Single colonies were isolated after 2 weeks of G418 selection, expanded, and examined for expression of Flag-tagged IκBα-DN in the absence of tetracycline.

EXAMPLE 5

Osteoclast Differentiation Assay

RAW264.7 cells were cultured in 24-well dishes at a density of 1×10⁴ cells per well and were allowed to adhere overnight. Medium was then replaced and the cells were treated with 100 ng/ml (~5 nM) RANKL. At day 5, cultures were stained for TRAP expression as described (Shevde et al., 2000) using an acid phosphatase kit, and the total number of TRAP-positive multinucleated osteoclasts (>3 nuclei) per well were counted.

EXAMPLE 6

Preparation of Nuclear Extracts for NF-κB Assay

Nuclear extracts were prepared as described earlier (Bharti et al., 2003). Briefly, 2×10⁶ RAW264.7 cells were washed with cold PBS, scraped, and suspended in 0.4 ml of hypotonic lysis buffer containing protease inhibitors for 30 min. The cells were then lysed with 12.5 μl of 10% Nonidet P-40. The homogenate was centrifuged, and supernatant containing the cytoplasmic extracts was stored frozen at −80° C. The nuclear pellet was re-suspended in 25 μl ice-cold nuclear extraction buffer. After 30 min of intermittent mixing, the extract was centrifuged, and supernatants containing nuclear extracts were secured. The protein content was measured by the Bradford method. If the extracts were not used immediately, they were stored at −80° C.

EXAMPLE 7

Electrophoretic Mobility Shift Assay for NF-κB

NF-κB activation was analyzed by electrophoretic mobility gel shift assay as described (Chaturvedi et al., 1994). In brief, 8 μg nuclear extracts prepared from curcumin-treated or untreated cells were incubated with ³²P end-labeled 45-mer double-stranded NF-κB oligonucleotide from human immunodeficiency virus-I long terminal repeat (5'-TTGTT1'-Acetoxychavicol AGGGACTTTCCGCTGGGGACTTTCCAG GGAGGCGTGG-3') (SEQ ID NO: 1) for 15 min at 37° C., and the DNA-protein complex resolved in a 6.6% native polyacrylamide gel. The radioactive bands from the dried gels were visualized and quantitated by the PhosphorImager (Molecular Dynamics, Sunnyvale, Calif.) using ImageQuant software.

EXAMPLE 8

Western Blotting

Thirty to fifty micrograms of cytoplasmic protein extracts were resolved on 10% SDS-PAGE gel. After electrophoresis, the proteins were electrotransferred to a nitrocellulose membrane, blocked with 5% nonfat milk, and probed with antibodies against either IκBα, phospho-IκBα, IKKα, IKKβ, or β-actin (1:3000) for 1 h. Thereafter, the blot was washed, exposed to HRP-conjugated secondary antibodies for 1 h, and finally detected by chemiluminescence (ECL, Amersham Pharmacia Biotech, Arlington Heights, Ill.).

EXAMPLE 9

IκBα Kinase Assay

The IκB kinase assay was performed by a modified method as described earlier (Manna et al., 2000). Briefly, 200 μg cytoplasmic extracts were immunoprecipitated with 1 μg of anti-IKKα and anti-IKKβ antibodies each, and the immune complexes so formed were precipitated with 0.01 ml of protein A/G-Sepharose beads for 2 hours. The beads were washed first with lysis buffer and then with the kinase assay buffer (50 mM HEPES pH 7.4, 20 mM MgCl₂, and 2 mM DTT). The immune complex was then assayed for kinase activity usinig kinase assay buffer containing 20 μCi [γ-³²P] ATP, 10 μM unlabeled ATP, and 2 μg/sample glutathione S-transferase-IκBα (amino acids 1-54). After incubation at 30° C. for 30 min, the mixture was boiled with 6×SDS sample buffer to stop the reaction. The reaction mixture was resolved on 12% SDS-PAGE. The radioactive bands of the dried gel were visualized and quantitated by PhosphorImager. To determine the total amount of IKKα and IKKβ in each sample, 60 μg of the cytoplasmic protein was resolved on a 7.5% acrylamide gel, and Western blotting was performed.

EXAMPLE 10

Curcumin Inhibits RANKL-Induced NF-κB Activation

To determine the effect of curcumin on RANKL-induced NF-κB activation in RAW 264.7 cells, these cells were first incubated with curcumin for 2 hours and then treated with RANKL, nuclear extracts were prepared and NF-κB activation was assayed by EMSA. RANKL activated NF-κB maximally within 15 minutes, and curcumin completely abrogated the RANKL-induced NF-κB activation (FIG. 1A).

Figure 1B:
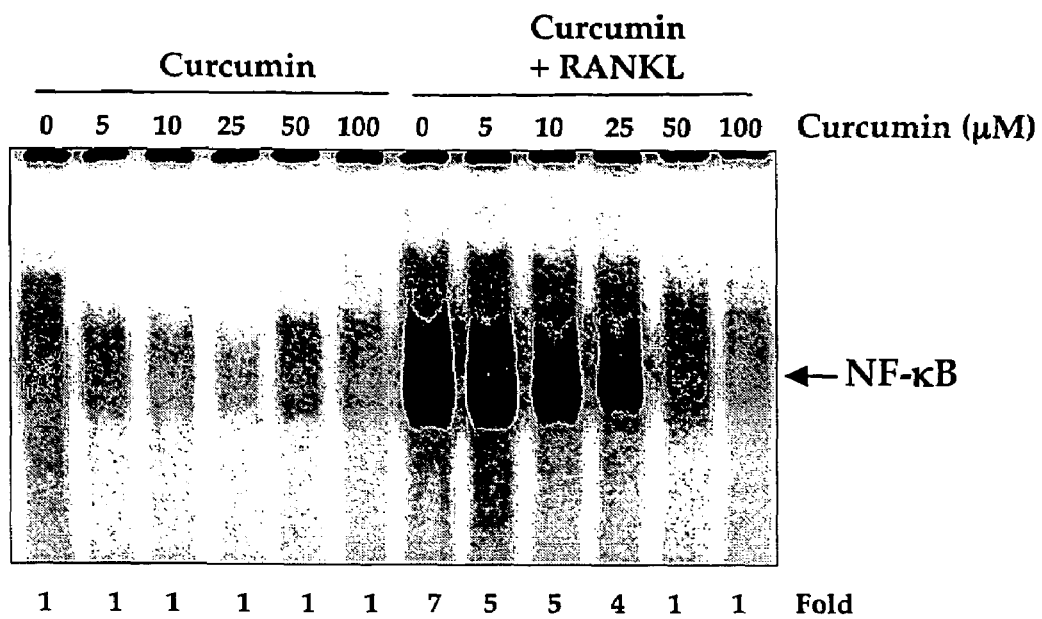
Figure 1C:
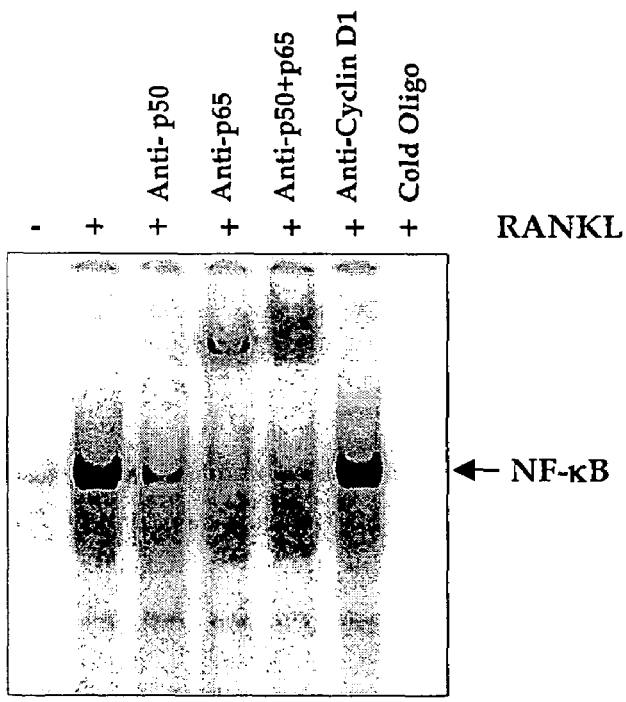
FIG. 1C shows that the binding of NF-κB is specific and consists of p50 and p65 subunits. Nuclear extracts were prepared from untreated RAW264.7 cell or the cells treated with RANKL, incubated for 15 minutes with different antibodies or unlabeled oligonucleotide probe, and then assayed for NF-κB by EMSA in 5% gel.

The inhibition of NF-κB by curcumin increased as the dose of curcumin was increased. Complete inhibition was observed at a 50 μM concentration of curcumin (FIG. 1B). Supershift assay of NF-κB/DNA probe binding showed that RANKL-activated NF-κB consisted of p65 and p50 subunits (FIG. 1C). Reaction mixtures containing antibodies to p50 or p65 showed either lesser NF-κB/DNA complex (with anti-p50) or a further shift in the NF-κB/DNA complex band (with anti-p65). The specificity of the RANKL-induced NF-κB/DNA complex was further confirmed by demonstrating that the binding was unaffected by irrelevant antibody (anti-cyclinD1) and was abolished by the presence of a 100-fold excess of unlabeled κB-oligonucleotides.

EXAMPLE 11

Curcumin Inhibits RANKL-Induced IκBα Phosphorylation and Degradation through Inhibition of IκB Kinase (IKK) Activity Activation of NF-κB by most agents requires phosphorylation and degradation of its inhibitory subunit IκBα. To investigate the mechanism involved in the inhibition of NF-κB activation by curcumin, the effects of curcumin treatment on the levels of IκBα by Western blotting was first examined.

Figure 2A:
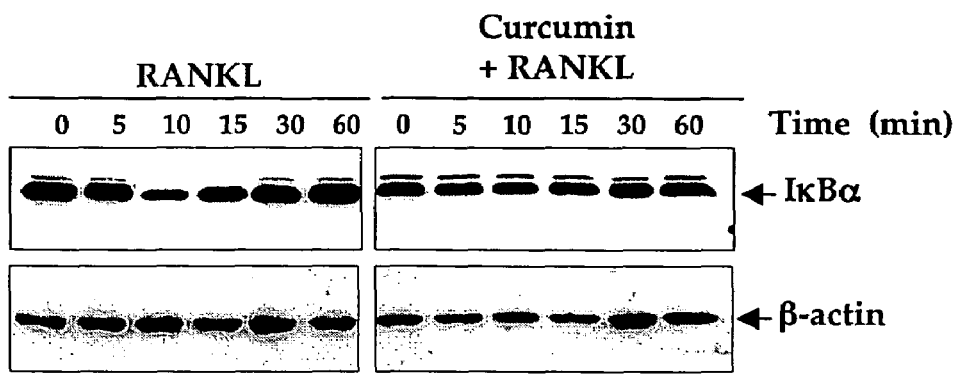
FIGS. 2A-C show that curcumin inhibits RANKL-induced IκBα phosphorylation and degradation through inhibition of IκB kinase activity. RAW 264.7 cells ($1 \times 10^6$ cells) were either incubated alone or in the presence of curcumin (50 μM) for 2 h and then treated with RANKL (10 nM) for the indicated times; and cytoplasmic extracts were prepared to examine the following.

The IκBα level dropped down within 10 min in the cells treated with RANKL, returned to normal within 60 min of treatment (FIG. 2A, left panel). In contrast, cells pretreated with curcumin showed no decrease in the RANKL-induced IκBα level (FIG. 2A, right panel).

Figure 2B:
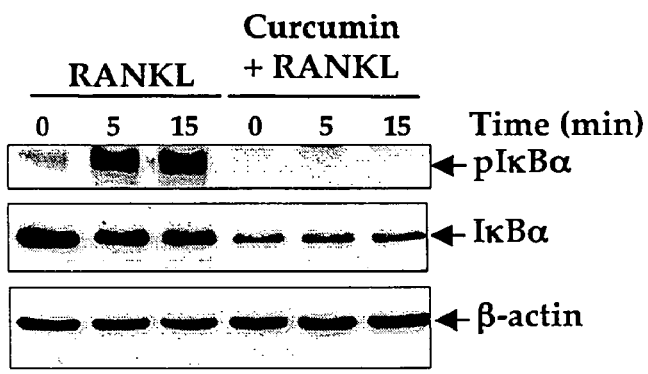

Next, the effect of curcumin on the RANKL-induced phosphorylation of IκBα, which occurs prior to its dissociation, ubiquitination and degradation (Rothwarf & Karin, 1999)

was investigated. Western blots for phospho-IκBα in FIG. 2B clearly indicate that RANKL induced IκBα phosphorylation in RAW cells and that curcumin eliminated the RANKL-induced phosphorylation. Treatment of cells with curcumin alone did not result in phosphorylation of IκBα.

Figure 2C:
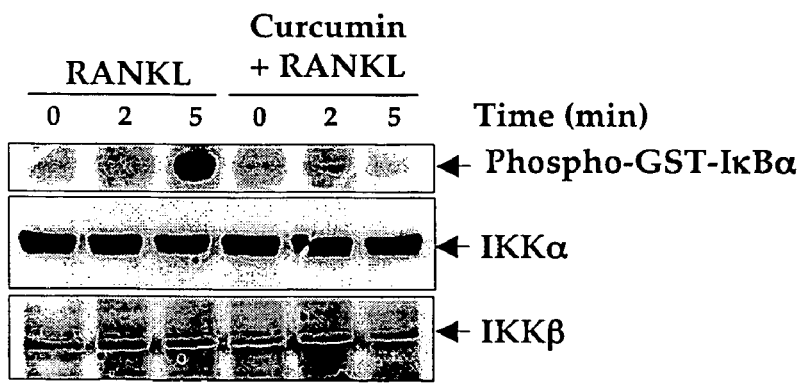

Since IKK phosphorylates IκBα (DiDonato et al., 1997), whether curcumin alters the activity or the levels of IKK was determined next. In in vitro IκB kinase assay, cells treated with RANKL showed a sharp rise in IKK activity as indicated by the phosphorylation of guggulsterone T-IκBα within 5 min. In contrast, cells pretreated with curcumin could not phosphorylate guggulsterone T-IκBα upon RANKL treatment (FIG. 2C, upper panel).

To determine if the apparent loss of IKK activity was due to the loss of IKK protein expression, the expression levels of the IKK subunits IKKα and IKKβ were examined by Western blotting. Results in FIG. 2C (middle and lower panel) clearly showed that curcumin treatment did not alter the expression of IKKα or IKKβ.

EXAMPLE 12

Curcumin Inhibits RANKL-Induced Osteoclastogenesis in RAW 264.7 Cells

Figure 3A:
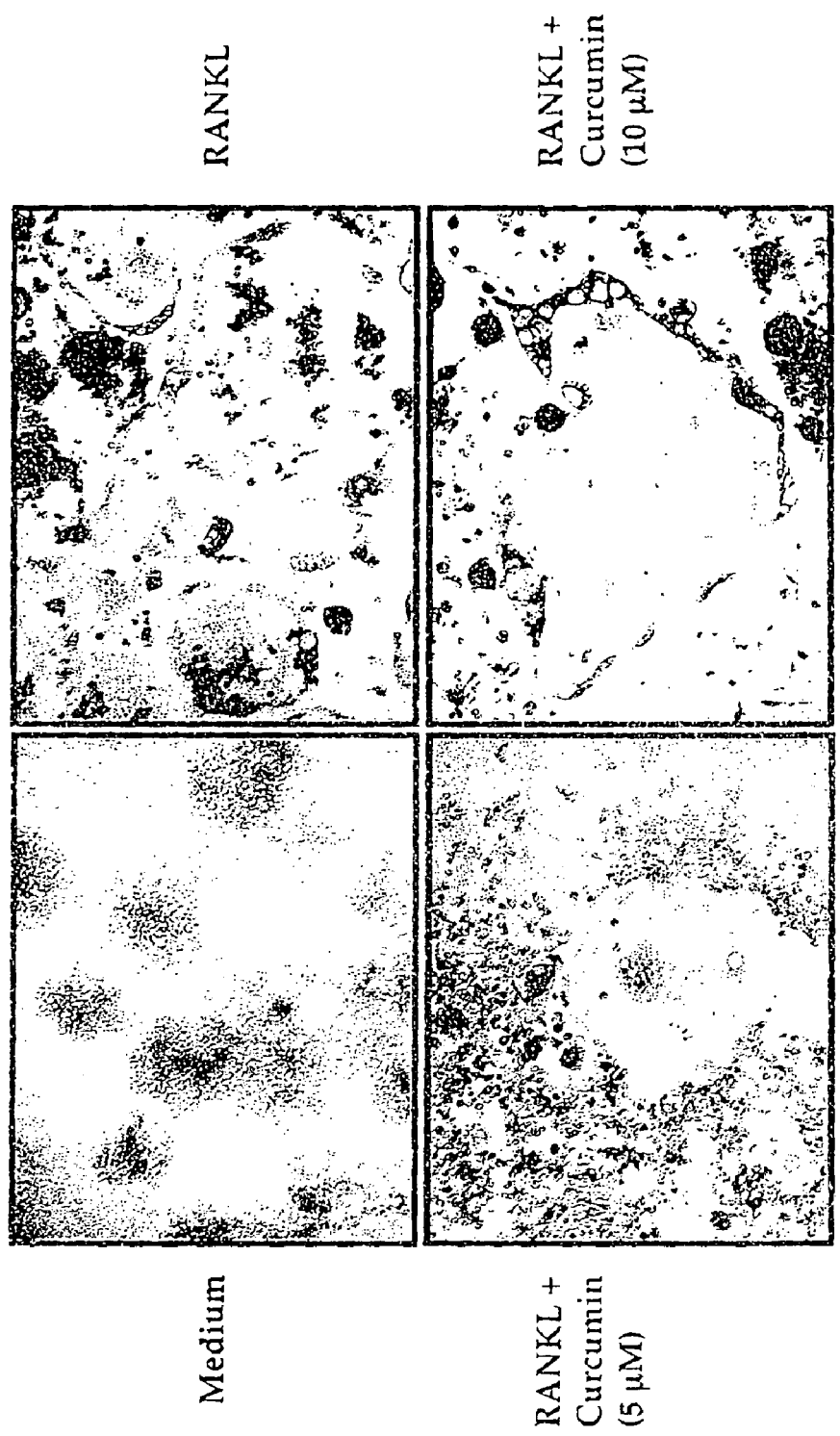
FIGS. 3A-B show that curcumin inhibits RANKL-induced osteoclastogenesis. RAW 264.7 cells ($1 \times 10^4$ cells) were incubated either alone or in the presence of RANKL (5 nM) without or with curcumin for 5 days and stained for TRAP expression.
Figure 3B:
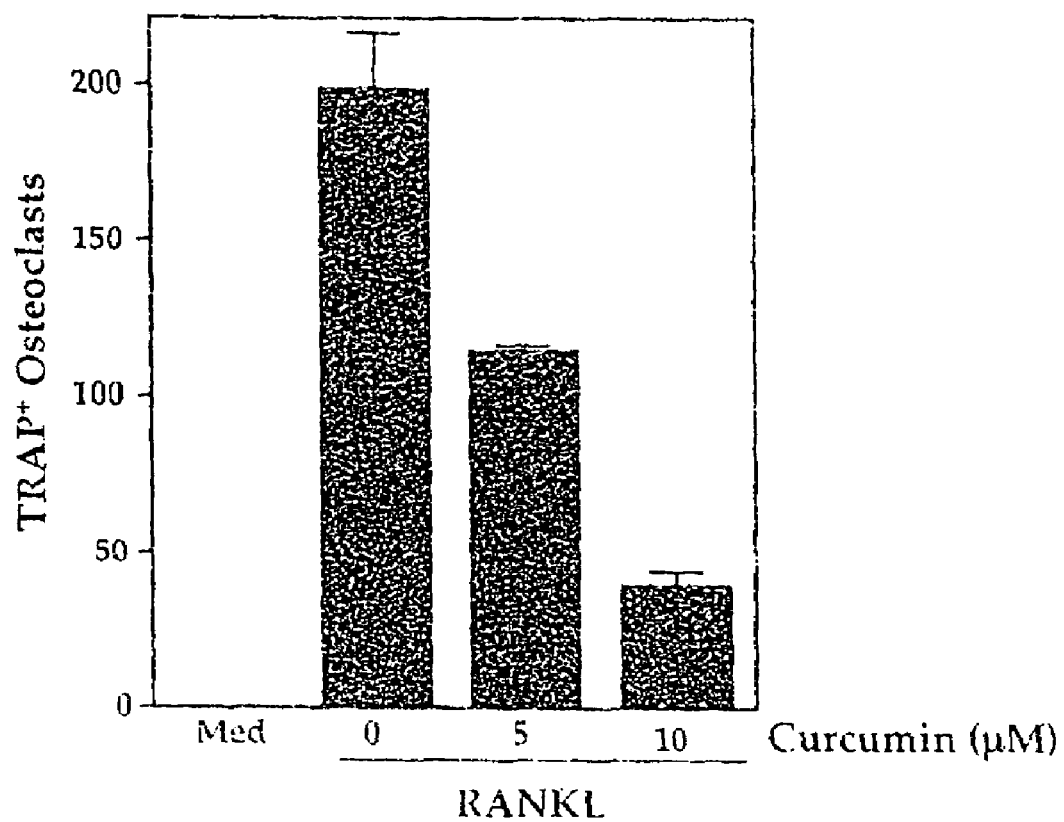

The effect of curcumin on osteoclastogenesis was investigated next. RAW 264.7 cells were incubated with different concentrations of curcumin in the presence of RANKL and allowed to grow and differentiate into osteoclasts. FIG. 3A illustrates that RANKL induced osteoclasts both in the presence and absence of curcumin. However, the number of osteoclasts decreased with increasing concentration of curcumin (FIG. 3B).

EXAMPLE 13

Curcumin Acts Early in the Pathway Leading to RANKL-Induced Osteoclastogenesis

It normally takes up to 5 days for RAW cells to differentiate into osteoclasts in response to RANKL. To determine how early in this pathway curcumin acts, the RAW 264.7 cells were treated with RANKL, curcumin was added on different days, and its effect on osteoclast formation was then checked.

Figure 4A:
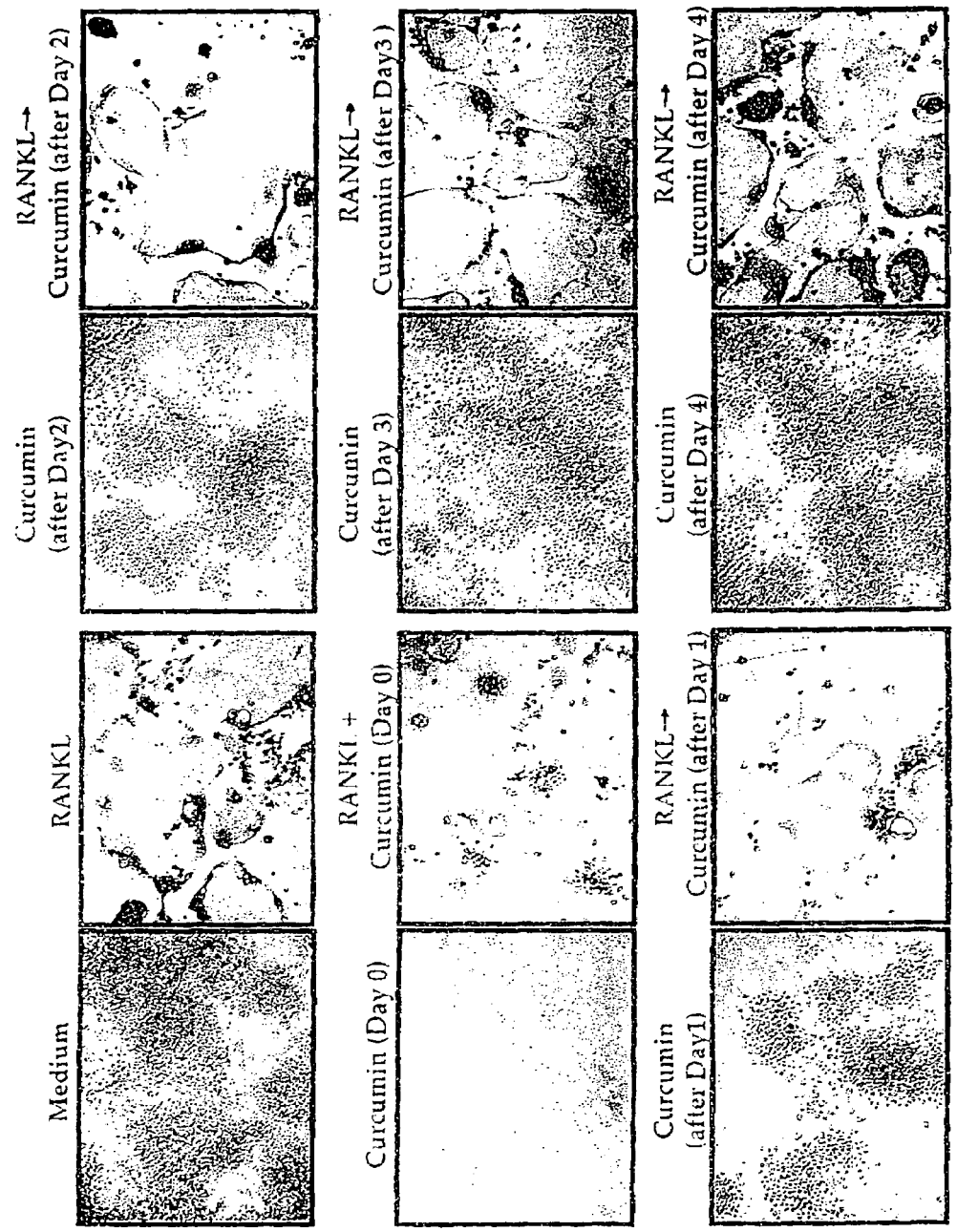
FIGS. 4A-B show that curcumin effectively inhibits RANKL-induced osteoclastogenesis 24 hours after stimulation. RAW 264.7 cells ($1 \times 10^4$ cells) were incubated either alone or in the presence of RANKL (5 nM), and curcumin (10 μM) was added at the same time or after indicated time periods. Cells were cultured for 5 days after RANKL treatment and stained for TRAP expression.
Figure 4B:
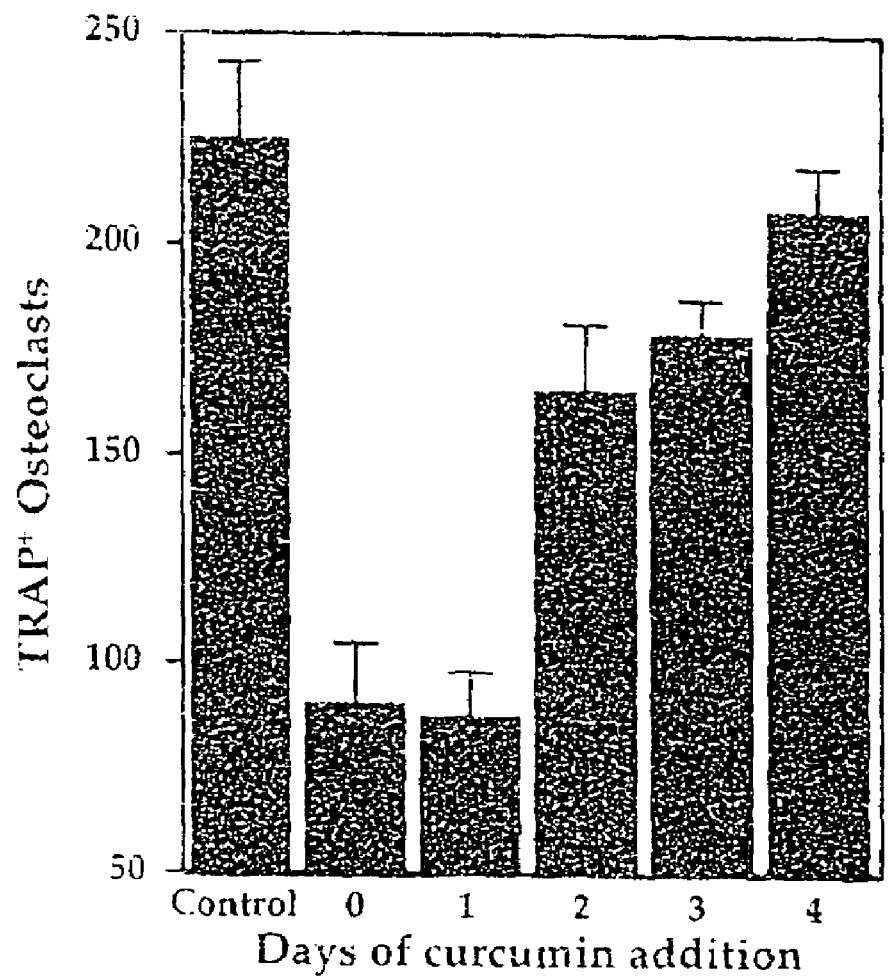

As shown in FIG. 4, curcumin inhibited osteoclastogenesis even when the cells were exposed 24 hours after the RANKL treatment (FIG. 4). However the inhibitory effect decreased significantly when cells were treated with curcumin 2 days after RANKL treatment.

EXAMPLE 14

Activation of NF-κB is Critical for RANKL-Induced Osteoclastogenesis

Besides NF-κB activation, RANKL is known to activate several other signals in the cell. It is possible that curcumin inhibits RANKL-induced osteoclastogenesis by suppressing signals other than NF-κB. To establish that curcumin suppressed osteoclastogenesis by inhibiting NF-κB activation, RAW 264.7 cells stably transfected with plasmid construct containing dominant-negative IκBα (IκBα-DN) were generated.

Figure 5A:
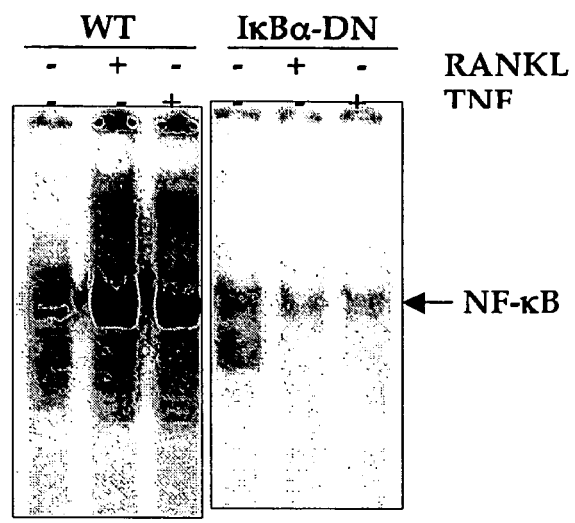
FIGS. 5A-B show RANKL-induced NF-κB activation is essential for RANKL-induced osteoclastogenesis. RAW 264.7 wild-type (WT) or IκBα-dominant negative stably transfected cells (IκBα-DN).
Figure 5B:
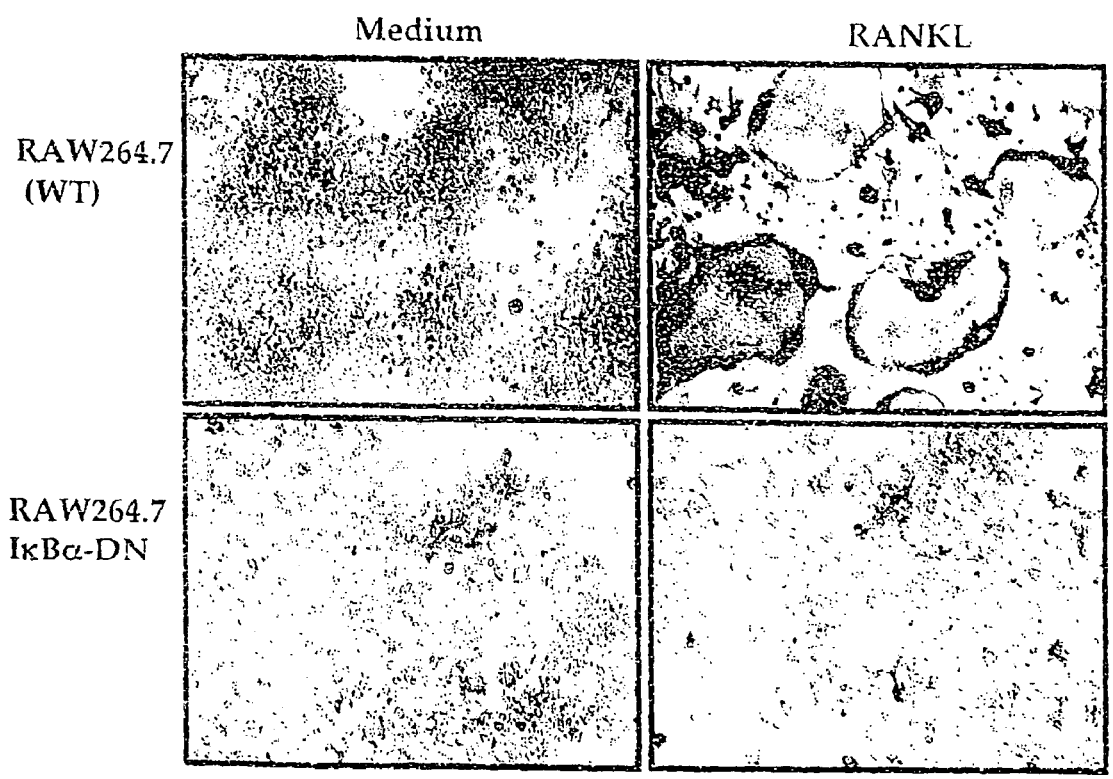

RANKL activated NF-κB in wild-type cells but not in IκBα-DN expressing cells (FIG. 5A). RANKL also failed to induce osteoclastogenesis in IκBα-DN expressing RAW cells (FIG. 5B) i.e., in cells that did not respond to NF-κB activation. These results suggest the critical role of NF-κB activation in RANKL-induced osteoclastogenesis.

In the present study, a homogeneous, clonal population of murine monocytic cells RAW 264.7 was used to define the direct effect of curcumin on osteoclast development induced by RANKL. The advantage of this system is that it does not contain any osteoblast/bone marrow stromal cells or cytokine like MCSF and allows one to focus on RANK signaling in pre-osteoclast cells.

In this study, curcumin inhibited RANKL-mediated NF-κB activation by inhibiting of IκB kinase activity, and it prevented osteoclast formation. Curcumin also inhibited the initial phase of cell growth by RANKL that is required for cell fusion and formation of a multi-nucleated cell. The critical role of NF-κB in RANKL-induced osteoclastogenesis was further confirmed by the use of dominant-negative IκBα.

These results indicate that RANKL activates NF-κB in osteoclastic precursor cells through the activation of IKK and subsequent IκBα phosphorylation and degradation. These results are in agreement with those of Wei et al. (Wei et al., 2001). Curcumin also inhibited RANKL-induced IKK activation, leading to the suppression of NF-κB activation. The mechanism of NF-κB activation induced by RANKL differs from that of TNF. For instance NIK, while required for RANKL-induced NF-κB activation (Uhlik et al., 1998), is dispensable for TNF-induced NF-κB activation (Russo et al., 2002). While curcumin has been shown to suppress TNF-induced IKK activation (Jobin et al., 1999; Plummer et al., 1999), this is the first report to suggest that curcumin can also suppress RANKL-induced NF-κB activation. This is in agreement with recent results that curcumin inhibits NF-κB activation, not by inhibiting upstream kinase to IKK but by inhibiting IKK directly (Bharti et al., 2003).

It was also found that the suppression of NF-κB activation by curcumin correlated with inhibition of osteoclastogenesis. Whether NF-κB activation is needed for osteoclastogenesis is controversial. While not all the cytokines that activate NF-κB induce osteoclastogenesis, other evidence suggests that activation of NF-κB is essential for osteoclast development (Boyce et al., 1999; Franzoso et al., 1997; Iotsova et al., 1997; Jimi et al., 1998; Kanegae et al., 1998; Wei et al., 2001). P50 and p52 double knockout mice showed defects in osteoclastogenesis and severe osteopetrosis (Iotsova et al., 1997). Results presented here show that NF-κB activation is critical for RANKL-induced osteoclastogenesis. It is possible that the inhibitory effect of curcumin on osteoclastogenesis is not mediated through suppression of NF-κB. This is unlikely, however, as RAW 264.7 cells transfected with a dominant-negative form of IκBα, which as a result could not activate NF-κB in response to RANKL, did not differentiate into multinucleated osteoclasts.

The present invention demonstrates that curcumin can inhibit the formation of osteoclasts. Curcumin has been shown to induce apoptosis in osteoclasts (Ozaki et al., 2000). It is possible that apoptotic effects of curcumin are responsible for suppression of osteoclastogenesis. This is unlikely, however, because the growth inhibitory effects of curcumin were reversed by RANKL. In addition, RAW cells, which failed to activate NF-κB, also failed to differentiate to osteoclasts in response to RANKL.

Stimulation of RANK also results in activation of c-Jun N-termirial kinase (JNK) activity along with NF-κB (Darnay et al., 1998). Recently, JNK has also been implicated in osteoclastogenesis (David et al., 2002). Curcumin can effectively inhibit JNK activity (Chen & Tan, 1998), so it is possible that JNK activity is also affected by curcumin in osteoclast precursors and may synergize with inhibition of NF-κB activation. That RAW cells, which lacked RANKL-induced NF-κB activation, failed to differentiate to osteoclasts suggests that NF-κB plays a major role.

Recently several cytokines have been reported that can suppress RANKL-induced osteoclastogenesis. These include IFN-β, IFN-γ, and IL-4, (Abu-Amer, 2001; Hayashi et al., 2002; Takayanagi et al., 2002; Takayanagi et al., 2000; Wei et al., 2001). All these cytokines mediate their effects through different mechanisms, e.g., IFN-γ induces the degradation of TRAF6 through ubiquitination-dependent pathway; IFN-β downregulates c-fos expression; and IL-4 downregulates NF-κB activation (Manna & Aggarwal, 1998) through a STAT6-dependent mechanism (Abu-Amer, 2001). These results show that curcumin inhibits osteoclastogenesis through inhibition of NF-κB.

As indicated by epidemiologic evidence, and by several phase I clinical trials, curcumin is pharmacologically safe in humans. Curcumin is being investigated for its anticancer activity in breast cancer and multiple myeloma and has provided encouraging results both in vitro and in vivo (Bharti et al., 2003; Shao et al., 2002; Singletary et al., 1996). That curcumin could be used in the treatment of secondary bone lesions associated with breast cancer and multiple myeloma and those associated with non malignant diseases like postmenopausal osteoporosis, Paget's disease and rheumatoid arthritis where severe osteolytic activity is observed has promise.

EXAMPLE 15

Figure 6A:
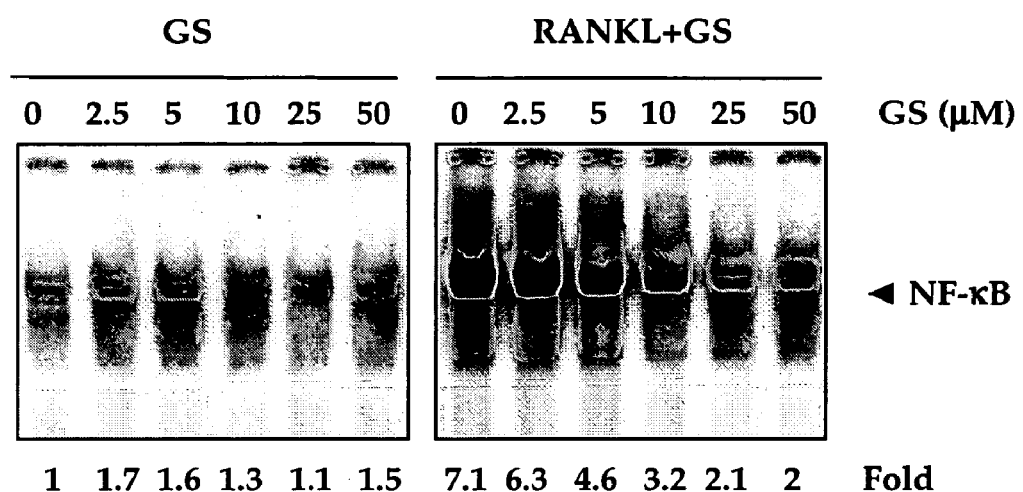
FIGS. 6A-B show that guggulsterone suppresses RANKL-induced NF-κB activation and IKK activation.
Figure 6B:
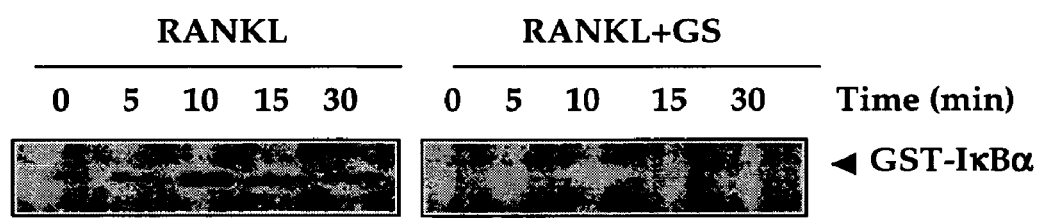

Guggulsterone (Guggulsterone) Suppresses RANKL-Induced Osteoclastogenesis through Suppression of NF-κB This study also demonstrated the effect of guggulsterone on RANKL-induced osteoclastogenesis. To determine if guggulsterone had any effect on RANKL-induced NF-κB activation, RAW264.7 cells were incubated with variable concentrations of guggulsterone for 4 h followed by treatment with RANKL for 25 minutes to activate NF-κB. The levels of NF-κB were then determined in samples treated with guggulsterone alone and those that were treated with RANKL and guggulsterone by EMSA (FIG. 6A). In the absence of RANKL, there was no NF-κB activation. Although RANKL activated NF-κB, the suppression of this activation increased as the concentration of guggulsterone increased. Maximal inhibition was observed at 50 μM concentration of guggulsterone. Further, to determine the effect of guggulsterone on IKK activation, RAW264.7 cells were incubated with guggulsterone for 4 hours followed by treatment with RANKL for different times. The IKK activity in samples treated with RANKL alone and with both RANKL and guggulsterone was determined by performing immune complex kinase assay (FIG. 6B). Cells treated with RANKL demonstrated a rise in IKK activity within 10 minutes. In contrast, cells pretreated with guggulsterone demonstrated absence of IKK activity upon RANKL treatment.

Figure 7A:
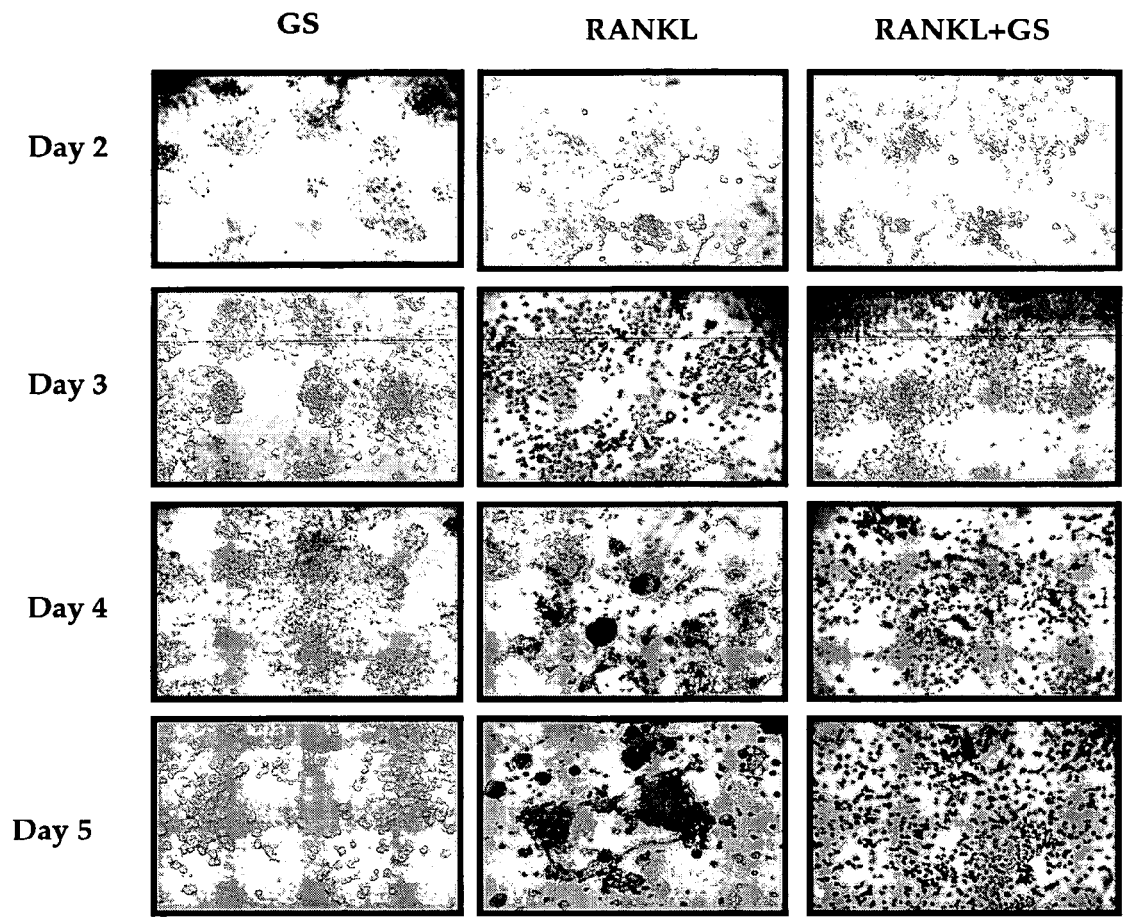
FIGS. 7A-B show that guggulsterone suppresses RANKL-induced osteoclastogenesis. RAW264.7 cells ($1 \times 10^4$ cells) were incubated with guggulsterone (5 μM) and RANKL (5 nM) for different days. The samples were then analyzed for osteoclastogenesis by TRAP assay.
Figure 7B:
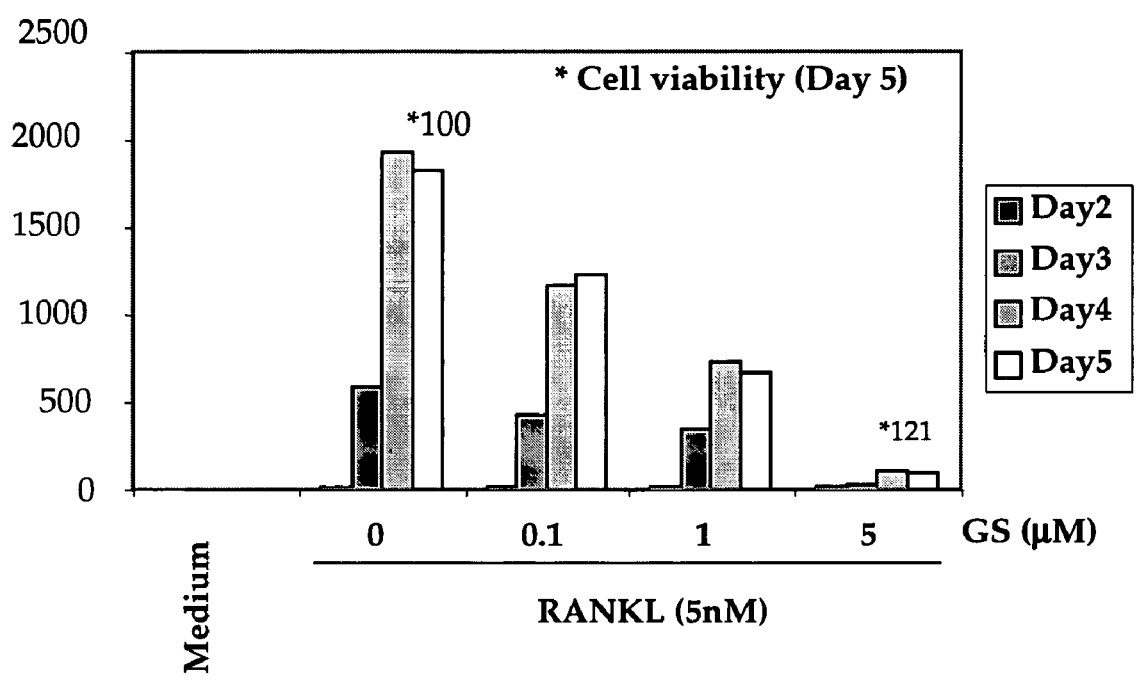

Next, the ability of guggulsterone to suppress RANKL-induced clastogenesis was examined by TRAP assay. RAW264.7 cells were incubated with guggulsterone and RANKL for different days. Osteoclastogenesis was then determined in samples that were incubated with guggulsterone alone, RANKL alone and with both RANKL and guggulsterone by TRAP assay. As shown in FIG. 7A, guggulsterone suppressed RANKL-induced osteoclastogenesis. As shown in FIG. 7B, the number of RANKL-induced TRAP positive cells decreased with increasing concentration of guggulsterone.

Figure 8A:
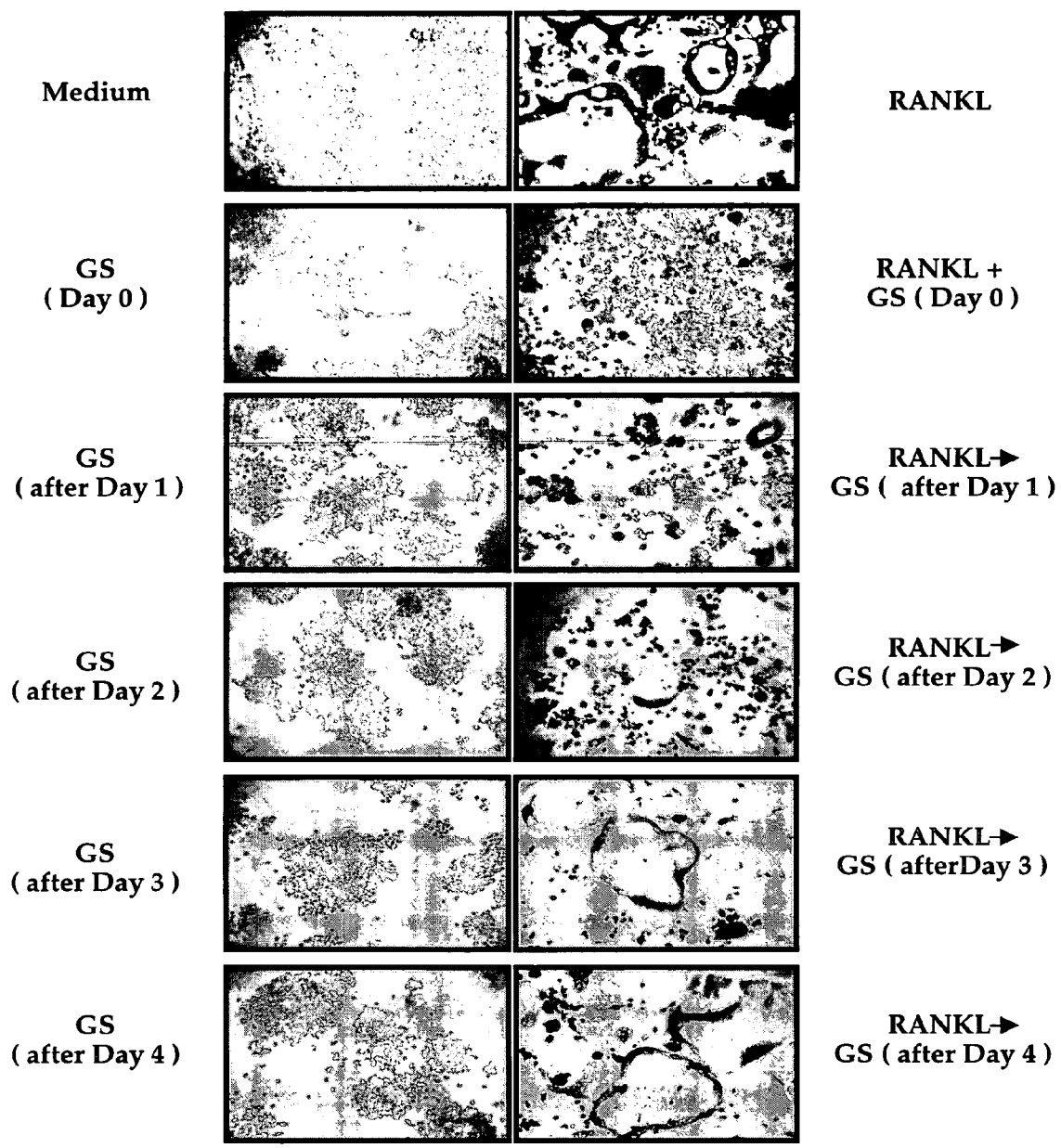
FIGS. 8A-B show that guggulsterone suppresses RANKL-induced osteoclastogenesis only when added together. RAW264.7 cells ($1 \times 10^4$ cells) were incubated with RANKL (5 nM) and guggulsterone (5 μM) was added on different days. The samples were then analyzed for osteoclastogenesis by TRAP assay.
Figure 8B:
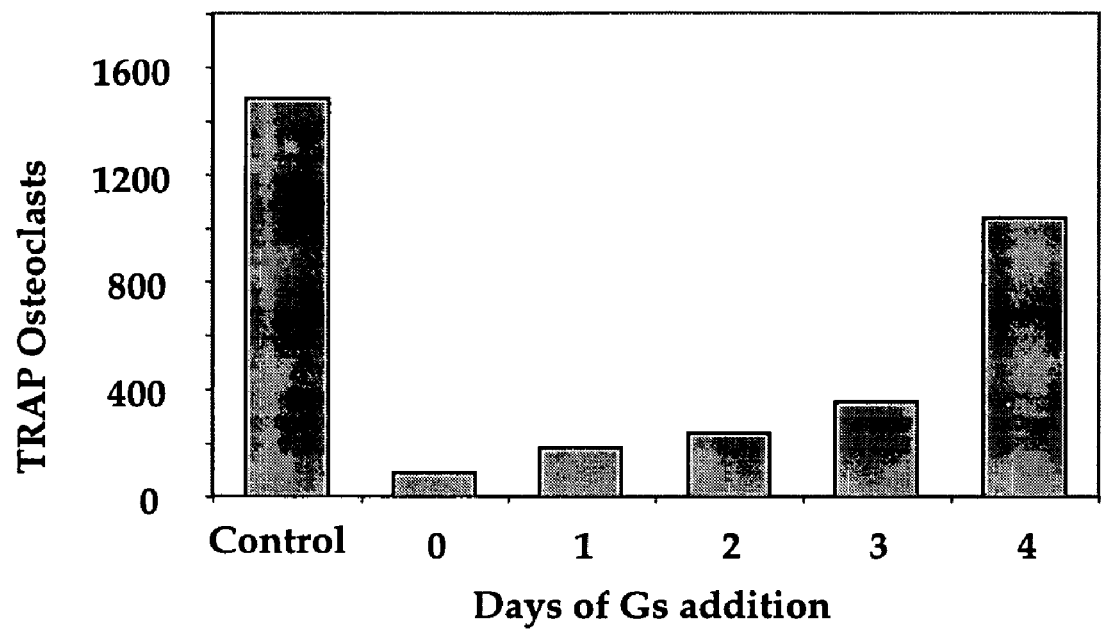

In order to determine the earliest time point at which guggulsterone could suppress RANKL-induced osteoclastogenesis, RAW264.7 cells were incubated with RANKL and guggulsterone was added on different days. Osteoclastogenesis was then analyzed in samples incubated with medium alone, with guggulsterone alone and with both RANKL and guggulsterone by TRAP assay. As shown in FIG. 8A, guggulsterone suppressed RANKL-induced osteoclastogenesis only when added together with RANKL. This finding was also confirmed by comparing the number of TRAP positive cells on different days of guggulsterone addition as shown in FIG. 8B.

EXAMPLE 16

1'-Acetoxychavicol Suppresses RANKL-Induced Osteoclastogenesis through Suppression of NF-κB This invention also demonstrated the effect of 1'-Acetoxychavicol on RANKL-induced osteoclastogenesis in a time-dependent and dose-dependent manner. To accomplish this, RAW264.7 cells were incubated with 1'-Acetoxychavicol and RANKL for different times (time-dependent, FIG. 9A) or with variable concentrations of 1'-Acetoxychavicol and constant concentration of RANKL for constant time (dose-dependent, FIG. 9B). The samples in both cases were analyzed for NF-κB by EMSA.

Figure 9A:
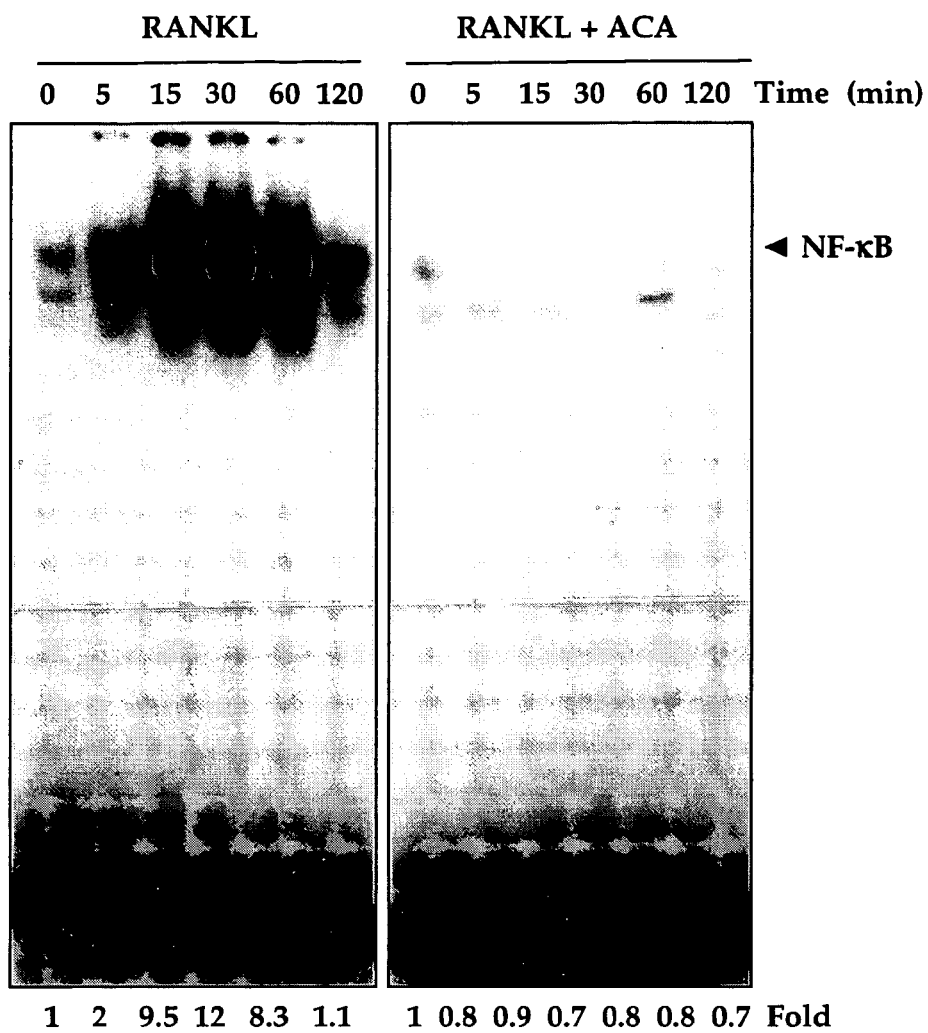
FIGS. 9A-B show that 1'-Acetoxychavicol suppresses RANKL-induced NF-κB activation in a time and dose dependent manner.
Figure 9B:
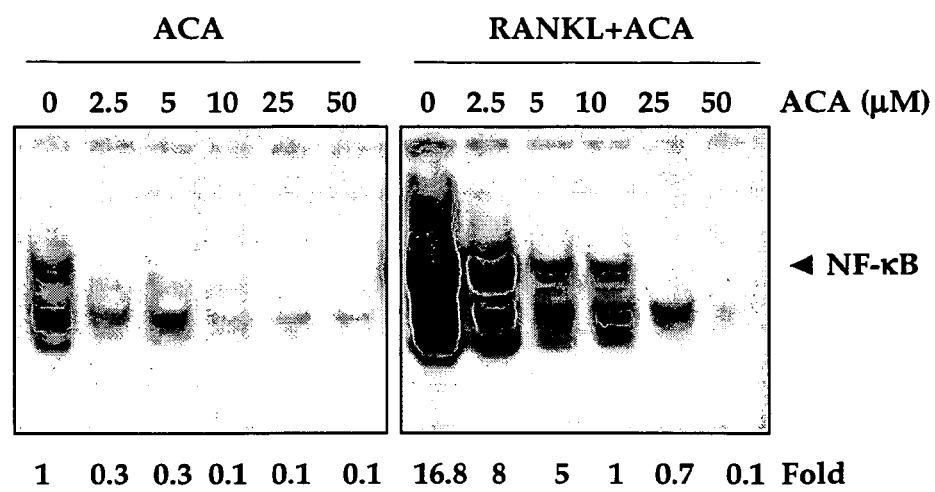

As shown in FIG. 9A, samples incubated with RANKL demonstrated increased NF-κB as early as 5-15 mins. However, 1'-Acetoxychavicol suppressed RANKL-induced NF-κB activation in time-dependent manner. Similarly as shown in FIG. 9B, 1'-Acetoxychavicol suppressed RANKL-induced NF-κB activation in a dose-dependent manner, with the maximal inhibition observed at 50 μM of 1'-Acetoxychavicol.

Figure 10A:
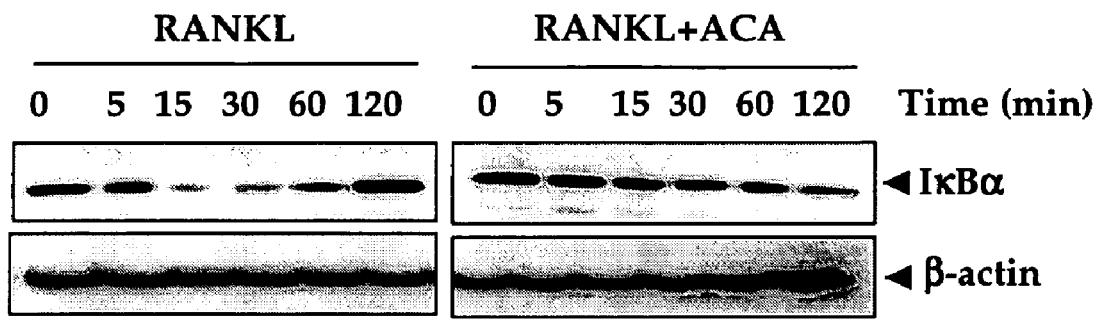
FIGS. 10A-B show that 1'-Acetoxychavicol suppresses RANKL-induced IκBα degradation and phosphorylation.
Figure 10B:
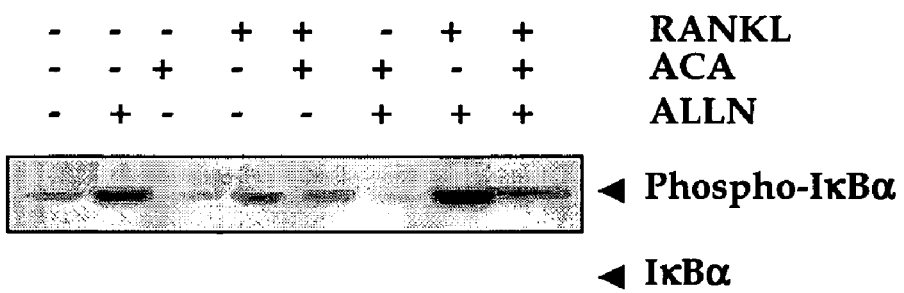

Further, the ability of 1'-Acetoxychavicol to suppress RANKL-induced IκBα degradation and phosphorylation was also examined. In order to determine the effect of 1'-Acetoxychavicol on IκBα degradation, RAW264.7 cells were incubated with 1'-Acetoxychavicol and RANKL for different times. As shown in FIG. 10A, samples incubated with only RANKL and those incubated with RANKL and 1'-Acetoxychavicol were analyzed for IκBα by western blot. The IκBα level dropped within 15 min in cells treated with RANKL alone but returned to normal within 60 minutes of treatment (FIG. 10A, left panel). In contrast, cells treated with both 1'-Acetoxychavicol and RANKL showed no decrease in the RANKL-induced IκBα level (FIG. 10B, right panel). Additionally, the effect of 1'-Acetoxychavicol on the RANKL-induced IκBα phosphorylation was examined. As shown in FIG. 10B, 1'-Acetoxychavicol suppressed the RANKL-induced. phosphorylation of IκBα.

Figure 11A:
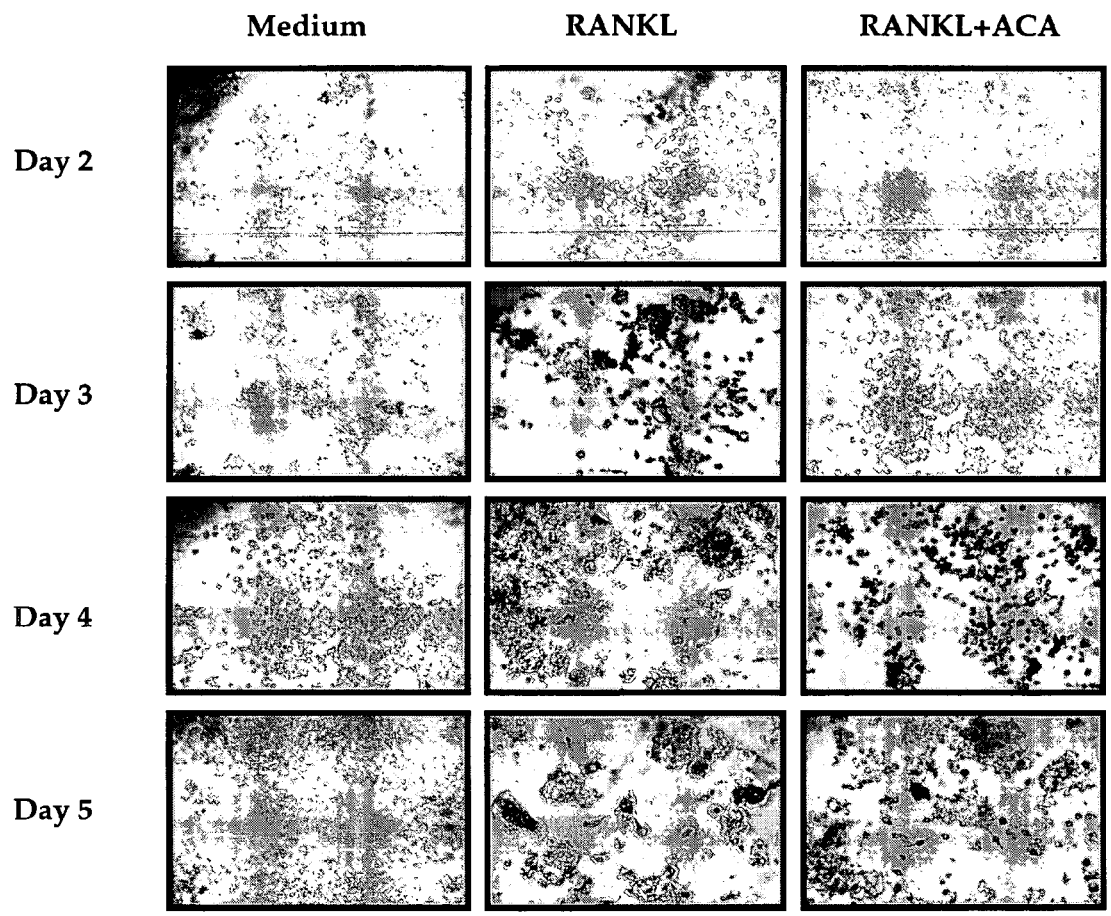
FIGS. 11A-B show that 1'-Acetoxychavicol suppresses RANKL-induced Osteoclastogenesis. RAW264.7 cells ($1 \times 10^4$ cells) were incubated with 1'-Acetoxychavicol (0.5 μM) and RANKL (5 nM) for different days. The samples were then analyzed for osteoclastogenesis by TRAP assay.
Figure 11B:
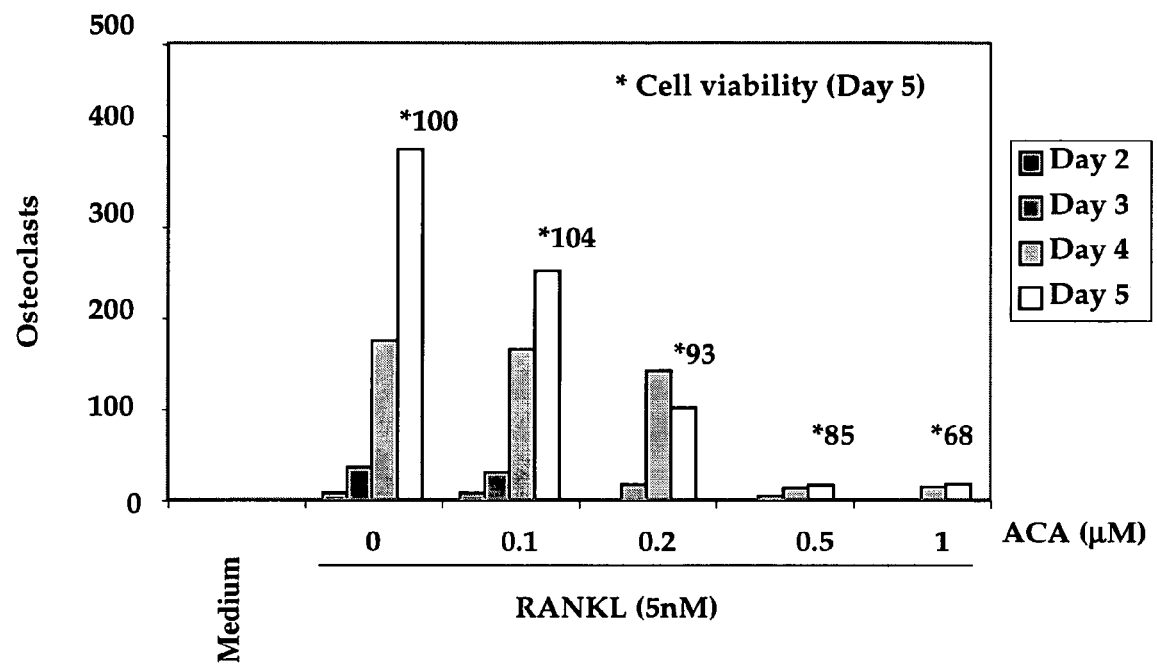

Next, the ability of 1'-Acetoxychavicol to affect RANKL-induced osteoclastogenesis was also examined. In order to accomplish this the RAW264.7 cells were incubated with 1'-Acetoxychavicol and RANKL for different days. Osteoclastogenesis was then analyzed in the cells that were incubated with no additions, with RANKL alone and with both RANKL and 1'-Acetoxychavicol for different days by TRAP assay. As shown in FIG. 11A, RANKL induced osteoclastogenesis in samples as early as day 3. In contrast, 1 '-Acetoxychavicol was able to suppress the RANKL-induced osteoclastogenesis in samples incubated for 3 days. However, osteoclasts were seen in samples that were incubated for longer time even in the presence of 1'-Acetoxychavicol. Further the effect of different concentrations of 1'-Acetoxychavicol on RANKL-induced TRAP positive cells was also assessed. As shown in FIG. 11B, the number of RANKL-induced osteoclasts decreased with increasing concentrations of 1'-Acetoxychavicol.

Figure 12A:
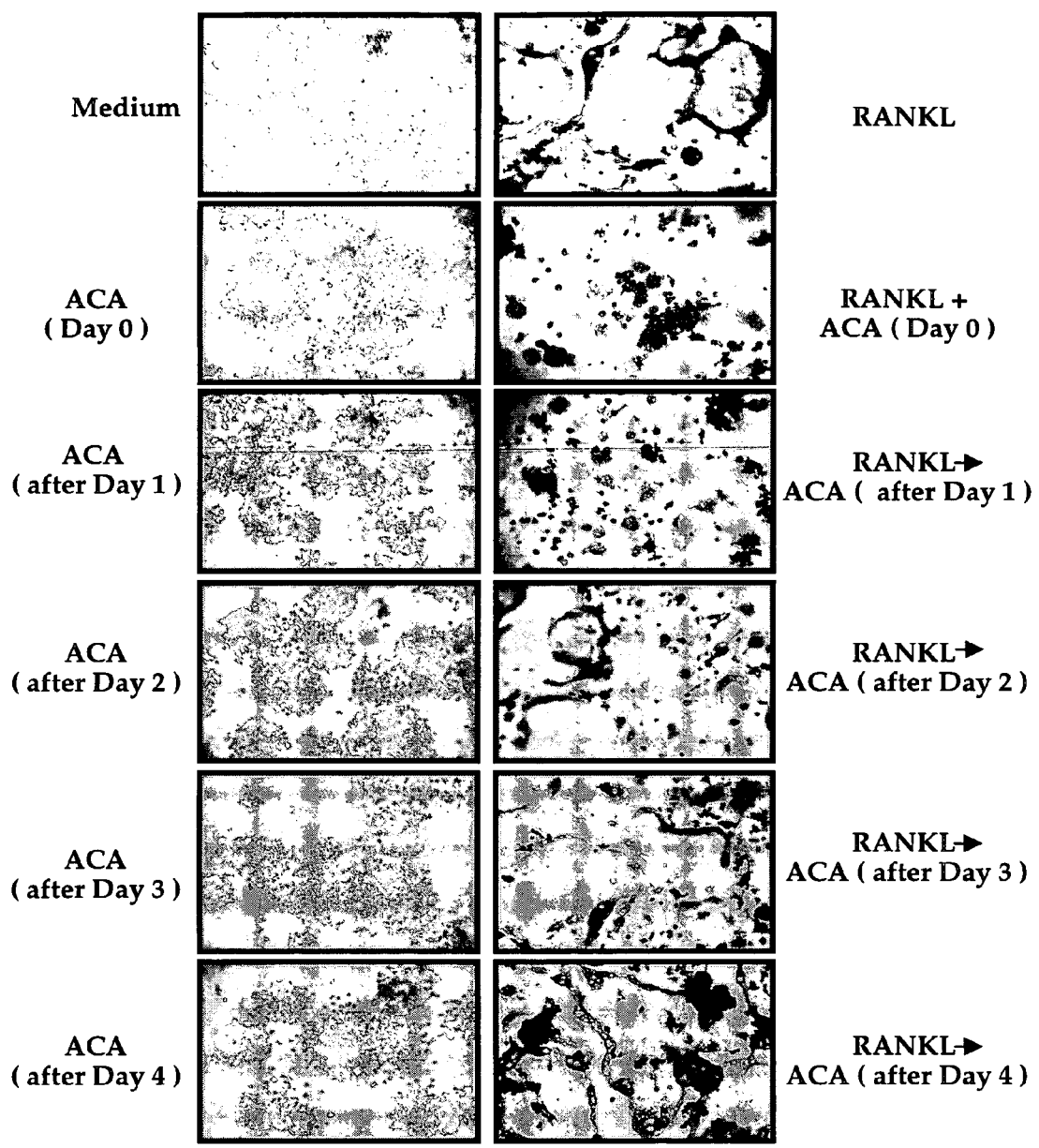
FIGS. 12A-B show that 1'-Acetoxychavicol suppresses RANKL-induced Osteoclastogenesis only when added together. RAW264.7 cells ($1 \times 10^4$ cells) were incubated with RANKL (5 nM) and 1'-Acetoxychavicol (0.5 μM) was added on different days. The samples were then analyzed for osteoclastogenesis by TRAP assay.
Figure 12B:
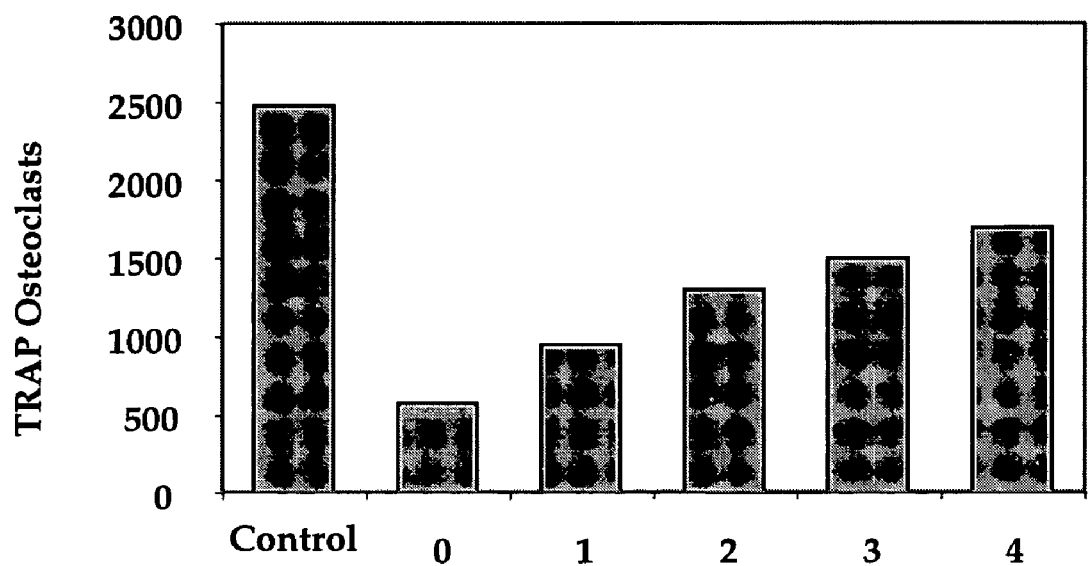

In order to determine the accurate time point for adding 1'-Acetoxychavicol to suppress RANKL-induced osteoclastogenesis, RAW264.7 cells were incubated with RANKL and 1'-Acetoxychavicol was added on different days. Osteoclastogenesis in samples incubated with medium alone, with 1'-Acetoxychavicol alone on different days and with RANKL and 1'-Acetoxychavicol on different days was analyzed by TRAP assay. As shown in FIG. 12A, 1'-Acetoxychavicol suppressed RANKL-induced osteoclastogenesis only when added together with RANKL. This finding was also confirmed by comparing the number of RANKL-induced TRAP positive cells on different days of 1'-Acetoxychavicol addition as shown in FIG. 12B.

EXAMPLE 17

Tumor Cells Induce Osteoclastogenesis through Expression of RANKL

The ability of tumor cells to induce osteoclastogenesis was also investigated in this study. Cells from head and neck squamous cell carcinoma and breast adenocarcinoma were used for this purpose. Briefly, RAW264.7 cells were incubated with different numbers of cells of head and neck squamous cell carcinoma (HN5, Fadu) or breast adenocarcinoma (MDA-MB-468, MCF-7) and then analyzed for osteoclastogenesis by TRAP assay.

Figure 13A:
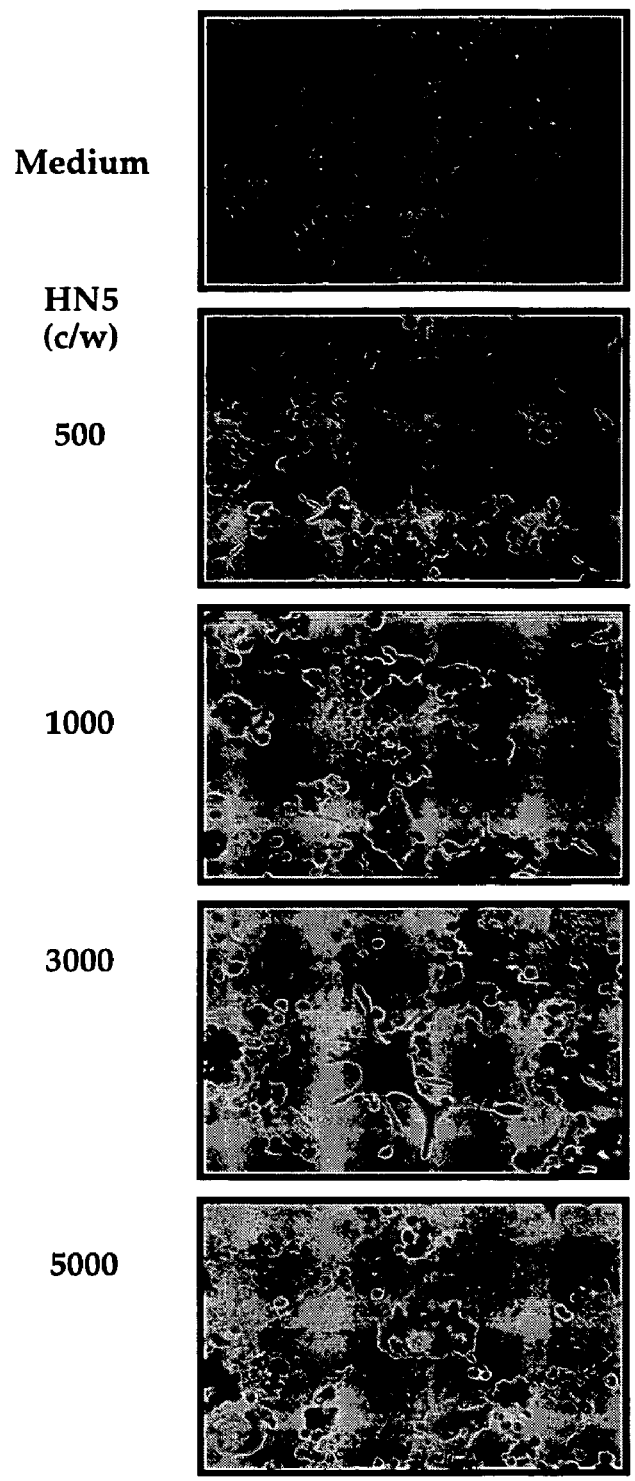
FIGS. 13A-D show that Head and Neck Squamous carcinoma cells induce osteoclastogenesis. RAW264.7 cells ($1 \times 10^4$ cells) were incubated with different numbers of HN5 cells or Fadu cells for five days. Osteoclastogenesis was then analyzed in these samples by TRAP assay.
Figure 13B:
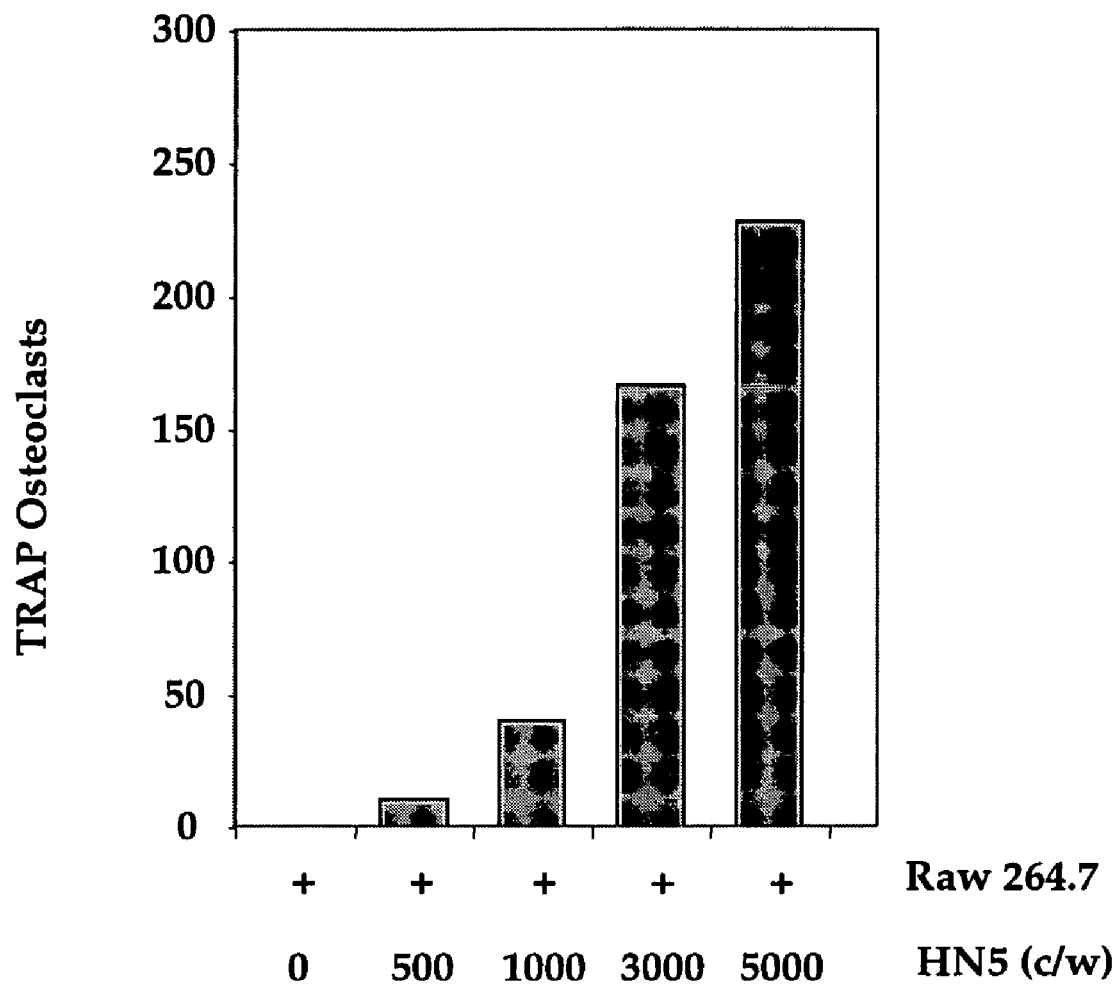
Figure 13C:
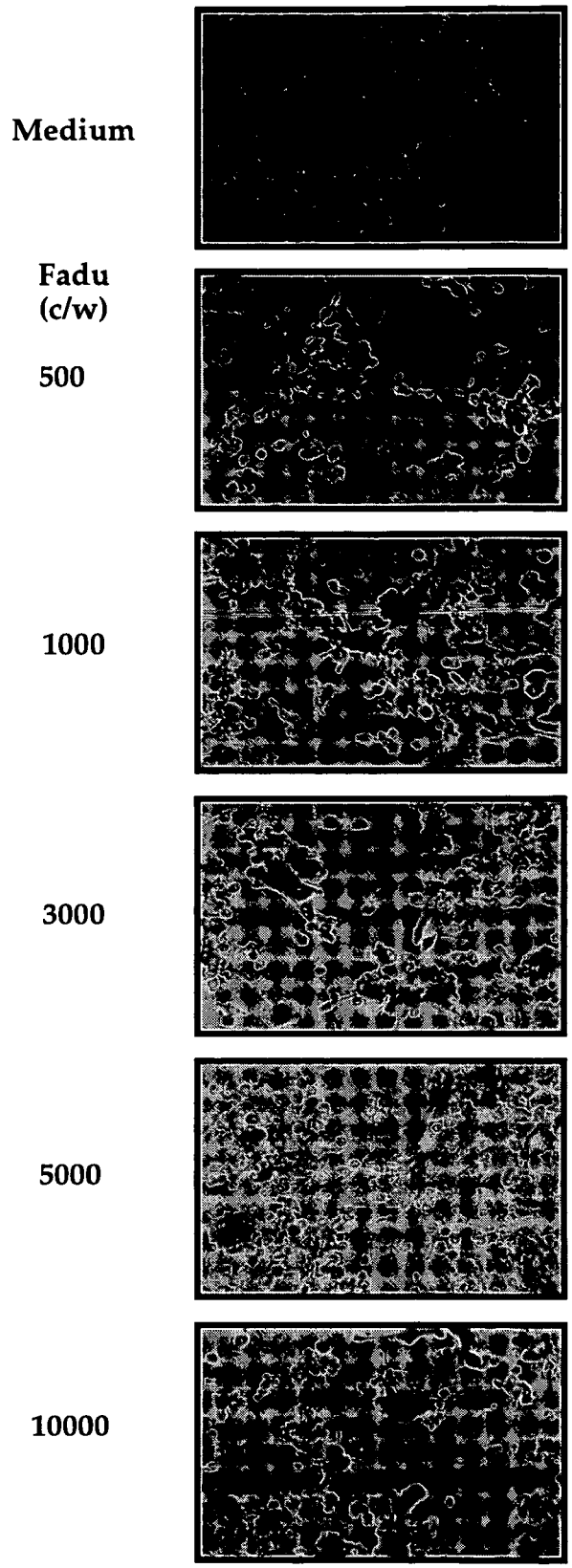
Figure 13D:
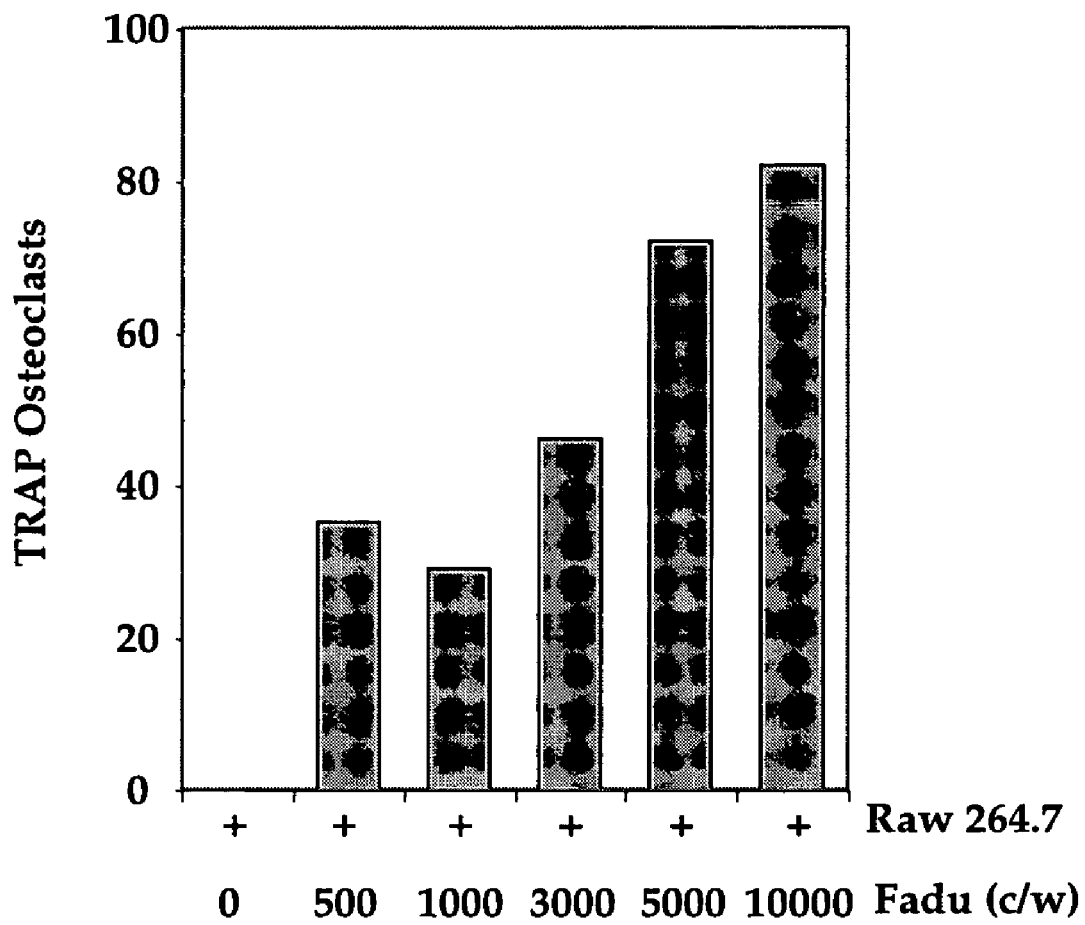
Figure 14D:
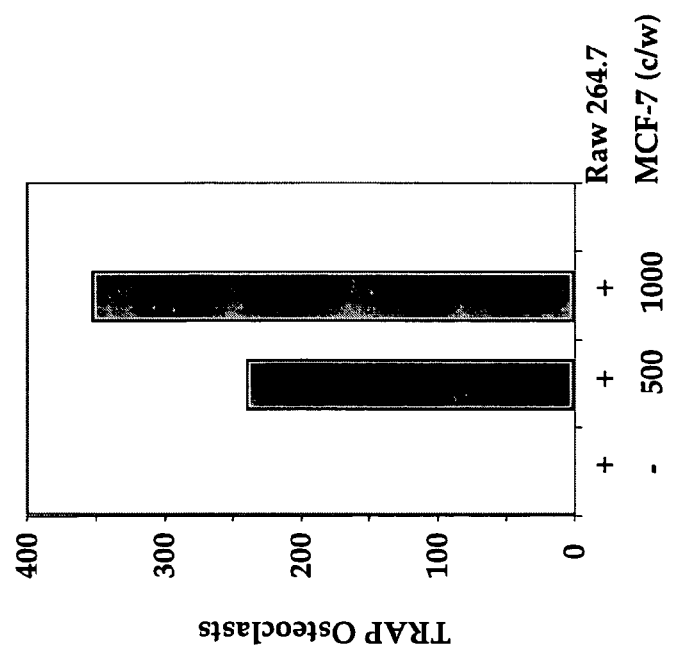
Figure 14C:
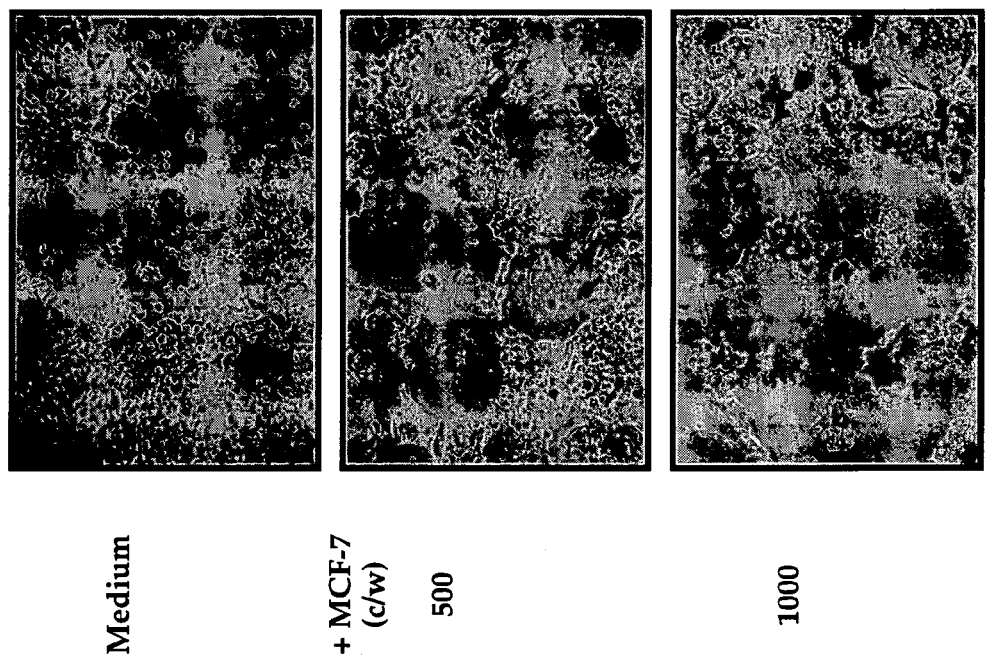
Figure 14F:
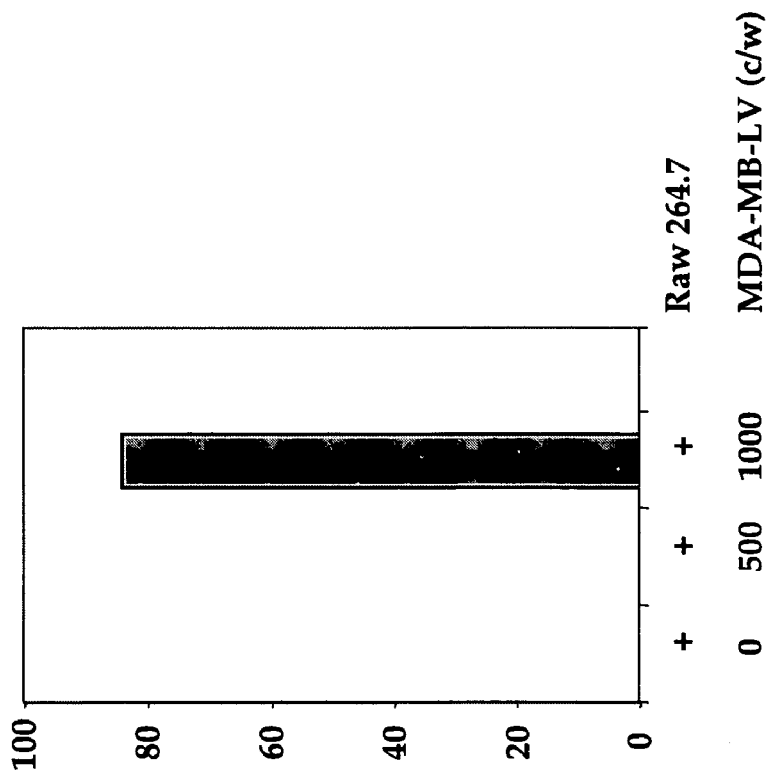
Figure 14E:
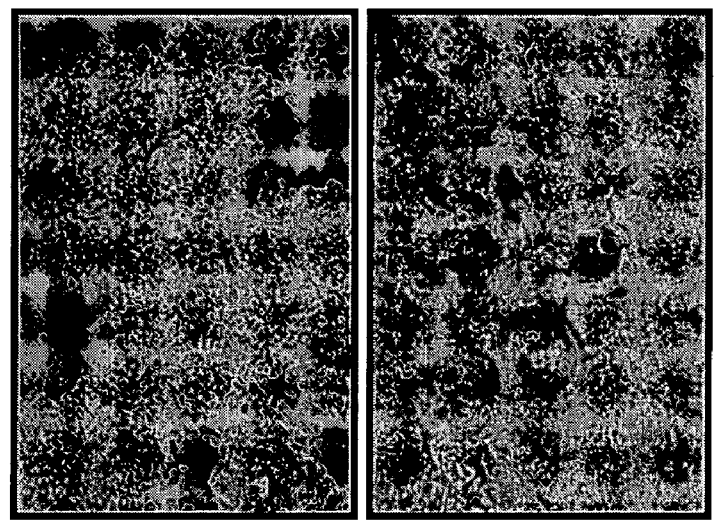

It was observed that increasing the numbers of HN5 (FIGS. 13A and 13B) or Fadu cells (FIGS. 13C and 13D) increased osteoclastogenesis and the number of TRAP-positive cells. This demonstrated the ability of head and neck squamous cell carcinoma cells to induce osteoclastogenesis. Similarly, increasing the numbers of MDA-MB-468 cells (FIGS. 14A and 14B) or MCF-7 cells (FIGS. 14C and 14D) or MDA-MB-LV cells (FIGS. 14E and 14F) increased osteoclastogenesis and the number of TRAP-positive cells. This demonstrated the ability of breast adenocarcinoma cells to induce osteoclastogenesis.

Figures 15A, 15B:
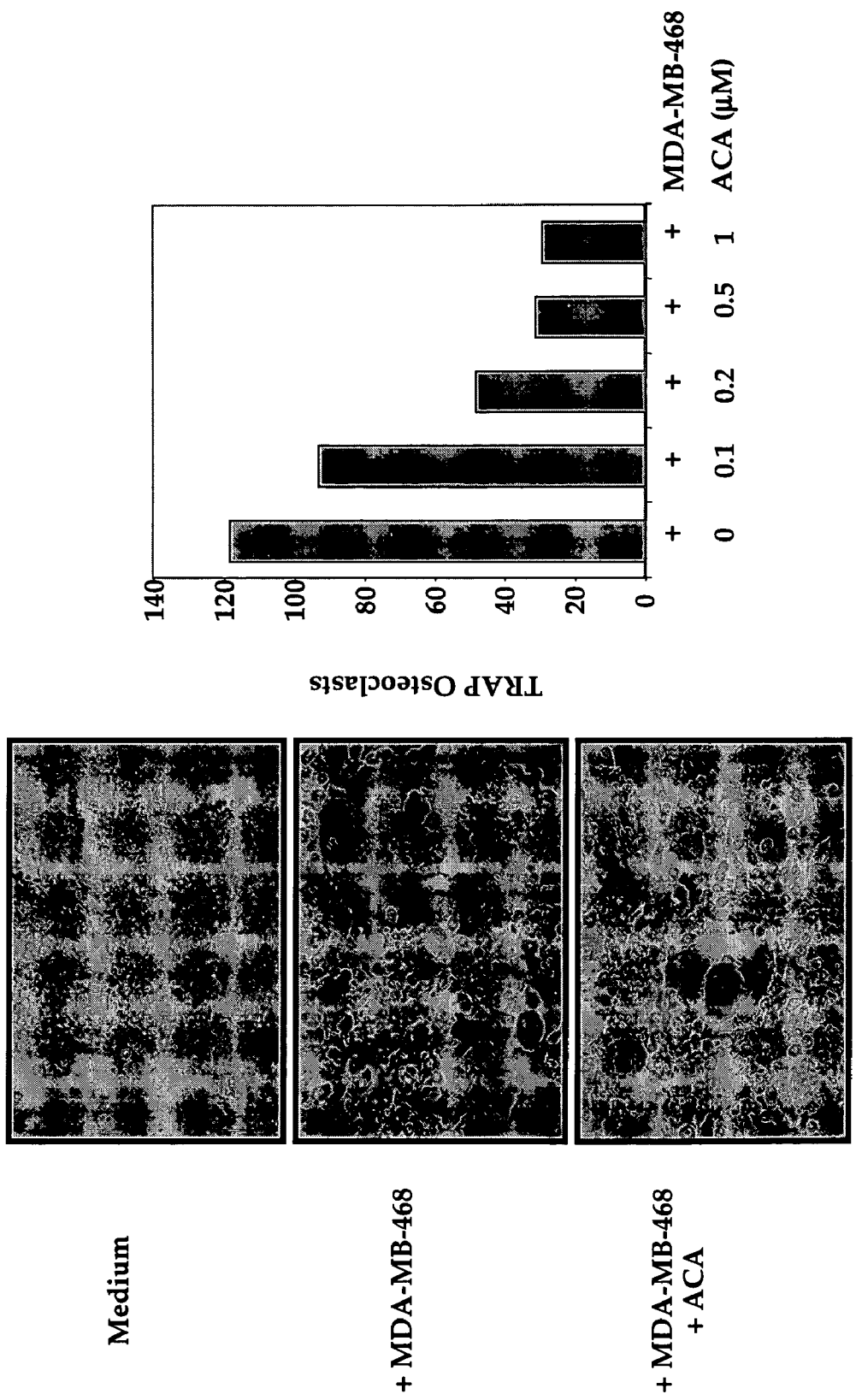
FIGS. 15A-D show that 1'-Acetoxychavicol suppresses breast adenocarcinoma cells-induced osteoclastogenesis. RAW264.7 cells ($1 \times 10^4$ cells) were incubated either with MDA-MB-468 cells ($1 \times 10^3$ cells) or with MCF-7 cells ($1 \times 10^3$ cells) in the presence of varying concentrations of 1'-Acetoxychavicol for five days and then analyzed for osteoclastogenesis by TRAP assay.
Figures 15C, 15D:
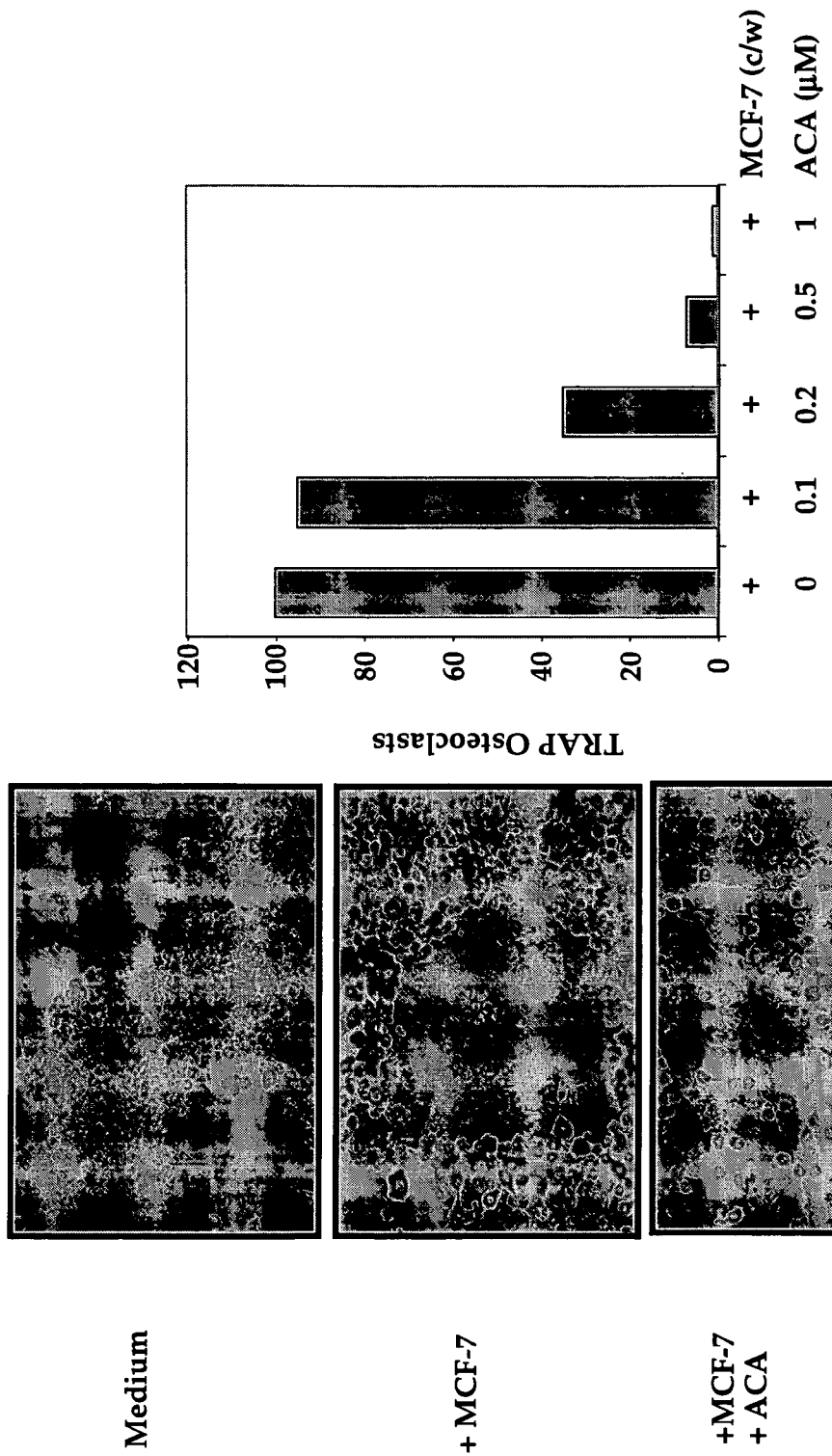

Since 1'-Acetoxychavicol was shown to suppress RANKL-induced osteoclastogenesis earlier in the study, the ability of 1'-Acetoxychavicol to suppress breast adenocarcinoma cells-induced osteoclastogenesis was also examined. Briefly, RAW264.7 cells were incubated with MDA-MB-468 or MCF-7 cells in presence of varying concentrations of 1'-Acetoxychavicol. 1'-Acetoxychavicol suppressed MDA-MB-468 cells (FIGS. 15A and 15B) or MCF-7 cells (FIGS. 15C and 15D) induced osteoclastogenesis. Additionally, the number of TRAP-positive cells also decreased as the concentration of 1'-Acetoxychavicol increased in cells incubated with MDA-MB-468 cells (FIG. 15B) or MCF-7 cells (FIG. 15D). These findings demonstrated that 1'-Acetoxychavicol suppressed breast adenocarcinoma cells-induced osteoclastogenesis.

Figures 16C, 16D:
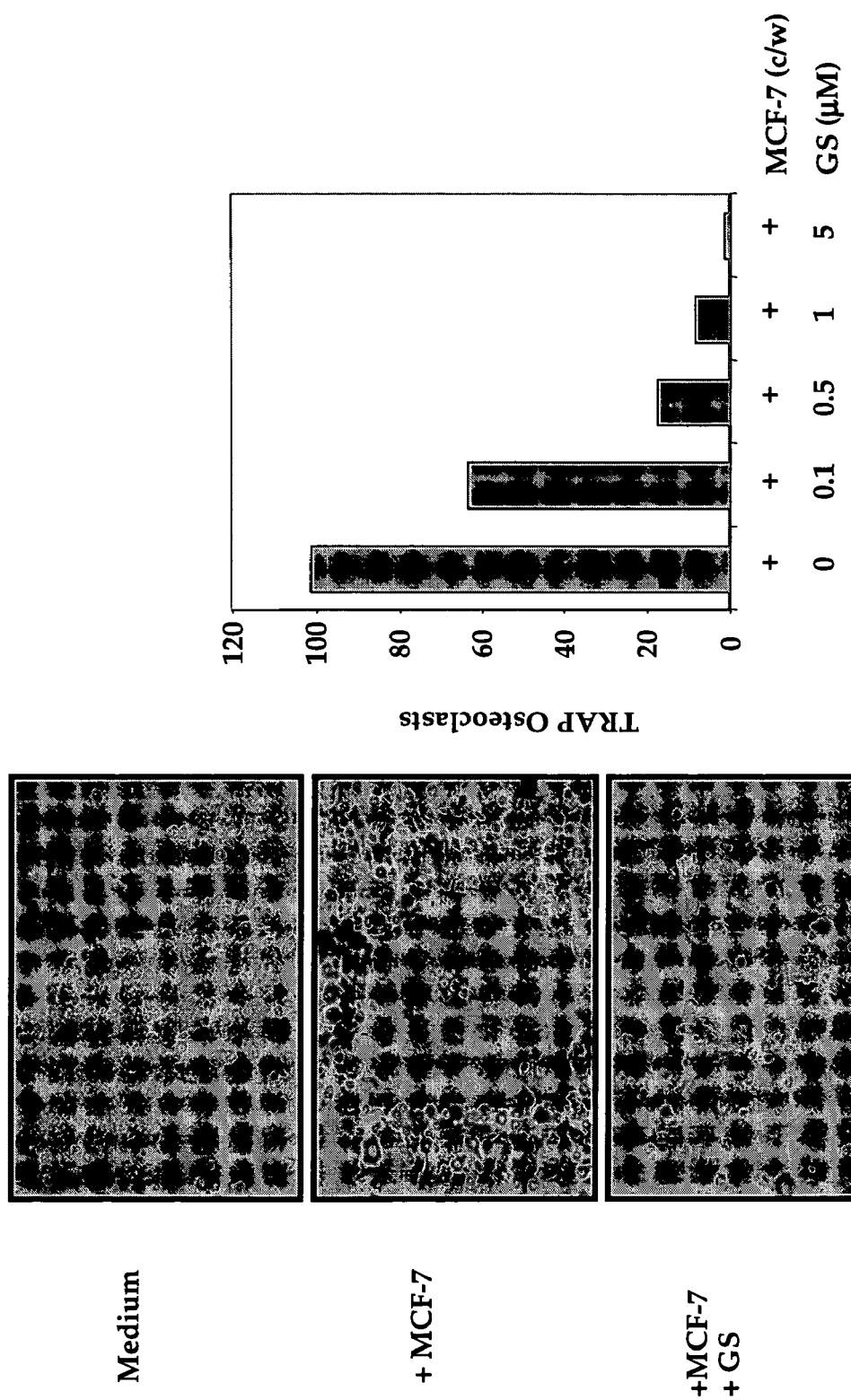

Further, since guggulsterone was shown to suppress RANKL-induced osteoclastogenesis earlier in the study, the ability of guggulsterone to suppress breast adenocarcinoma cells-induced osteoclastogenesis was also examined. RAW264.7 cells were incubated with MDA-MB-468 or MCF-7 cells in presence of varying concentrations of guggulsterone. Guggulsterone suppressed MDA-MB-468 cells (FIGS. 16A and 16B) or MCF-7 cells (FIGS. 16C and 16D) induced osteoclastogenesis. Additionally, the number of TRAP-positive cells also decreased as the concentration of guggulsterone increased in cells incubated with MDA-MB-468 cells (FIG. 16B) or MCF-7 cells (FIG. 16D). These findings demonstrated that guggulsterone suppressed breast adenocarcinoma cells-induced osteoclastogenesis.

Figure 17:
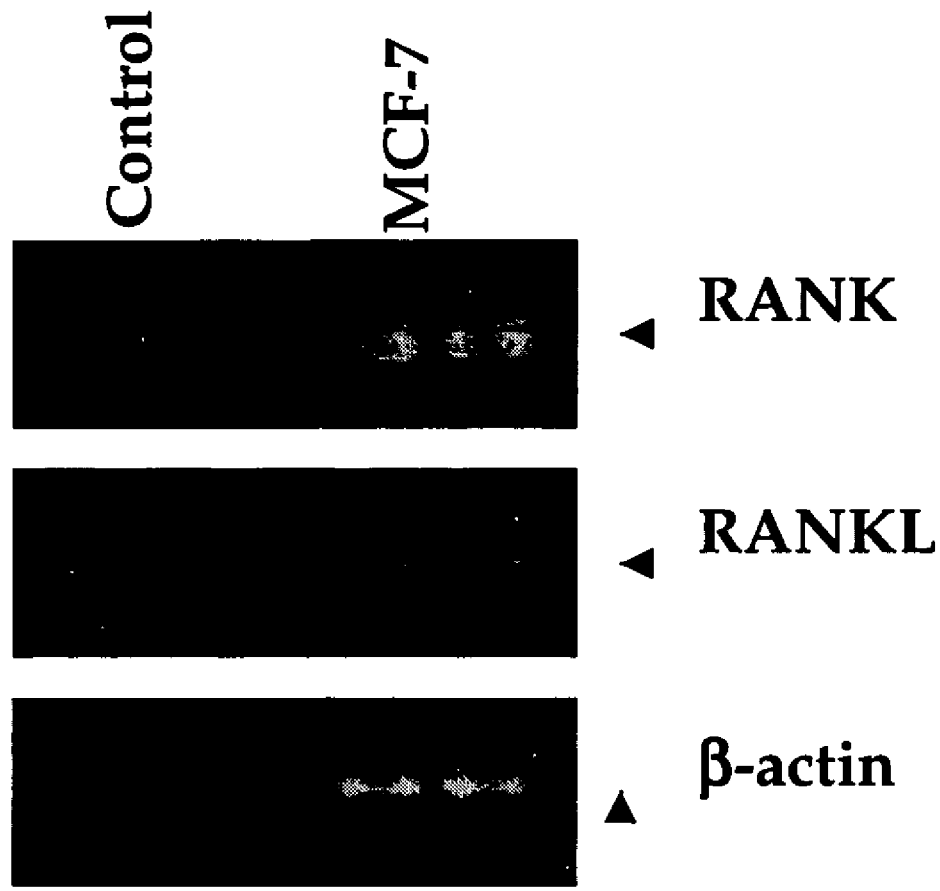
FIG. 17 show that MCF-7 breast cancer cells express both RANK and RANKL by RT-PCR.

Since both 1'-Acetoxychavicol and guggulsterone that were shown earlier in the study to suppress RANKL-induced osteoclastogenesis also suppressed osteoclastogenesis induced by tumor cells, the expression of RANK and RANKL were examined on MCF-7 cells by RT-PCR. MCF-7 cells expressed both RANK and RANKL (FIG. 17). These findings indicate that tumor cells induced osteoclastogenesis through the expression of RANKL, which was suppressed by guggulsterone and 1'-Acetoxychavicol.

The following references were cited herein:
Abu-Amer, Y. (2001). *J Clin Invest*, 107, 1375-85.
Bharti, et al., (2003). *Blood*, 101, 1053-62.
Boyce, et al., (1999). *Bone*, 25, 137-9.
Brockman, et al., (1995). *Mol Cell Biol*, 15, 2809-18.
Bucay, et al., (1998). *Genes Dev*, 12, 1260-8.
Chaturvedi, et al., (1994). *J Biol Chem*, 269, 14575-83.
Chen, Y. R. & Tan, T. H. (1998). *Oncogene*, 17, 173-8.
Cheng, et al., (2001). *Anticancer Res*, 21, 2895-900.
Dai et al., (2002). *Blood*, 99, 111-20.
Darnay, et al., (1999). *Ann Rheum Dis*, 58 Suppl 1, 12-I13.
Darnay, et al., (1998). *J Biol Chem*, 273, 20551-5.
Darnay, et al., (1999). *J Biol Chem*, 274, 7724-31.
David, et al., (2002). *J Cell Sci*, 115, 4317-25.
DiDonato, et al., (1997). *Nature*, 388, 548-54.
Franzoso, et al., (1997). *Genes Dev*, 11, 3482-96.
Haridas, et al., (1998). *J Immunol*, 160, 3152-62.
Hayashi, et al., (2002). *J Biol Chem*, 277, 27880-6.
Hsu, et al., (1999). *Proc Nati Acad Sci U S A*, 96, 3540-5.
Iotsova, et al., (1997). *Nat Med*, 3, 1285-9.
Jimi, et al., (1998). *J Biol Chem*, 273, 8799-805.
Jobin, et al., (1999). *J Immunol*, 163, 3474-83.
Kanegae, et al., (1998). *Nature*, 392, 611-4.
Kong, et al., (1999). *Nature*, 397, 315-23.
Kumar, et al., (1998). *Biochem Pharmacol*, 55, 775-83.
Lacey, et al., (1998). *Cell*, 93, 165-76.
Lee, et al., (1997). *Immunity*, 7, 703-13.
Li, J., et al., (2000). *Proc Natl Acad Sci U S A*, 97, 1566-71.
Lomaga, M. A., et al., (1999). *Genes Dev*, 13, 1015-24.
Manna, S. K. & Aggarwal, B. B. (1998). *J Biol Chem*, 273, 33333-41.
Manna, et al., (2000). *J Immunol*, 165, 5962-9.
Matsumoto, et al., (2000). *J Biol Chem*, 275, 31155-61.
Ozaki, et al., (2000). *Biochem Pharmacol*, 59, 1577-81.
Pan, et al., (2000). *Biochem Pharmacol*, 60, 1665-76.
Plummer, et al., (1999). *Oncogene*, 18, 6013-20.
Rodan, G. A. & Martin, T. J. (2000). *Science*, 289, 1508-14.
Rothwarf, D. M. & Karin, M. (1999). *SciSTKE*, 1999, RE1.
Russo, et al., (2002). *Am J Physiol Cell Physiol*, 283, C347-57.
Shao, et al., (2002). *Int J Cancer*, 98, 234-40.
Shevde, et al., (2000). *Proc Natl Acad Sci USA*, 97, 7829-34.
Singh, S. & Aggarwal, B. B. (1995). *J Biol Chem*, 270, 24995-5000.
Singh, et al., (1996). *J Biol Chem*, 271, 31049-54.
Singletary, et al., (1996). *Cancer Lett*, 103, 137-41.
Takayanagi, et al., (2002). *Nature*, 416, 744-9.
Takayanagi, et al., (2000). *Nature*, 408, 600-5.
Teitelbaum, S. L. (2000). *Science*, 289, 1504-8.
Tiffee, et al., (1999). *Calcif Tissue Int*, 65, 53-8.
Udagawa, et al., (1990). *Proc Natl Acad Sci USA*, 87, 7260-4.
Uhlik, et al., (1998). *J Biol Chem*, 273, 21132-6.
Wei, et al., (2001). *Endocrinology*, 142, 1290-5.
Wong, et al., (1998). *J Biol Chem*, 273, 28355-9.
Xing, et al., (2001). *Genes Dev*, 15, 241-53.
Zhang, et al., (2001). *J Biol Chem*, 276, 563-8.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of inhibiting the formation of osteoclasts in an individual, comprising identifying an individual in need of an inhibitor of the formation of osteoclasts and administering to said individual a pharmacologically effective dose of diferuloylmethane, guggulsterone, 1'-Acetoxychavicol or an analogue thereof, wherein the individual has multiple myeloma, breast cancer, rheumatoid arthritis, or Paget's disease and the formation of osteoclasts is inhibited.

2. The method of claim 1, wherein RANKL-mediated NF-κB activation in said individual is inhibited.

3. The method of claim 2, wherein said inhibition of RANKL-mediated NF-κB activation is by inhibition of IκB kinase activity.

4. The method of claim 1, wherein said individual is administered diferuloylmethane in a concentration of from about 0.01 mg/kg of said individual's body weight to about 100 mg/kg of said individual's body weight.

5. The method of claim 1, wherein said individual is administered guggulsterone in a concentration of from about 0.01 mg/kg of said individual's body weight to about 100 mg/kg of said individual's body weight.

6. The method of claim 1, wherein said individual is administered 1'-Acetoxychavicol in a concentration of from about 0.01 mg/kg of said individual's body weight to about 100 mg/kg of said individual's body weight.

7. A method of reducing osteolytic activity and bone loss in an individual, comprising identifying an individual in need of reduction of osteolytic activity and bone loss and administering to said individual a pharmacologically effective dose of diferuloylmethane, guggulsterone, 1'-Acetoxychavicol or an analogue thereof, wherein the individual has multiple myeloma, breast cancer, rheumatoid arthritis, or Paget's disease and osteolytic activity and bone loss in the individual is reduced.

8. The method of claim 7, wherein said individual is administered diferuloylmethane in a concentration of from about 0.01 mg/kg of said individual's body weight to about 100 mg/kg of said individual's body weight.

9. The method of claim 7, wherein said individual is administered guggulsterone in a concentration of from about 0.01 mg/kg of said individual's body weight to about 100 mg/kg of said individual's body weight.

10. The method of claim 7, wherein said individual is administered 1'-Acetoxychavicol in a concentration of from about 0.01 mg/kg of said individual's body weight to about 100 mg/kg of said individual's body weight.

11. The method of claim 1, wherein the individual has multiple myeloma.

12. The method of claim 1, wherein the individual has Paget's disease.

13. The method of claim 1, wherein the individual is administered a pharmacologically effective dose of diferuloylmethane.

14. The method of claim 7, wherein the individual has multiple myeloma.

15. The method of claim 7, wherein the individual has Paget's disease.

16. The method of claim 7, wherein the individual is administered a pharmacologically effective dose of diferuloylmethane.

* * * * *

SEQUENCE LISTING

<160> NUMBER OF SEQ ID NOS: 1

<210> SEQ ID NO 1
<211> LENGTH: 45
<212> TYPE: DNA
<213> ORGANISM: Human immunodeficiency virus
<220> FEATURE:
<223> OTHER INFORMATION: NF-kappB oligonucleotide

<400> SEQUENCE: 1
ttgttacaag ggactttccg ctggggactt tccagggagg cgtgg    45